US007910344B2

(12) United States Patent
Kruus et al.

(10) Patent No.: US 7,910,344 B2
(45) Date of Patent: Mar. 22, 2011

(54) PROTEINS HAVING TYROSINASE ACTIVITY

(75) Inventors: Kristiina Kruus, Espoo (FI); Emilia Selinheimo, Espoo (FI); Karin Autio, Espoo (FI); Johanna Buchert, Espoo (FI); Markku Saloheimo, Helsinki (FI); Raija Lantto, Klaukkala (FI)

(73) Assignee: Valtion teknillinen tutkimuskeskus, Espoo (FI)

( * ) Notice: Subject to any disclaimer, the term of this patent is extended or adjusted under 35 U.S.C. 154(b) by 394 days.

(21) Appl. No.: 11/815,988

(22) PCT Filed: Feb. 9, 2006

(86) PCT No.: PCT/FI2006/050055
§ 371 (c)(1),
(2), (4) Date: Oct. 11, 2007

(87) PCT Pub. No.: WO2006/084953
PCT Pub. Date: Aug. 17, 2006

(65) Prior Publication Data
US 2009/0203882 A1 Aug. 13, 2009

(30) Foreign Application Priority Data

Feb. 10, 2005 (FI) .................................. 20055059

(51) Int. Cl.
*C12N 9/02* (2006.01)
(52) U.S. Cl. .................................................. 435/189
(58) Field of Classification Search ............... None
See application file for complete search history.

(56) References Cited

U.S. PATENT DOCUMENTS

| 5,340,734 A | 8/1994 | Della-Cioppa et al. |
| 6,242,221 B1 | 6/2001 | Robinson |

FOREIGN PATENT DOCUMENTS

| JP | 10174586 | 6/1998 |
| JP | 2001157586 | 6/2001 |
| JP | 2004201545 | 7/2004 |
| WO | 0214595 | 2/2002 |
| WO | 03007728 | 1/2003 |

OTHER PUBLICATIONS

Van Gelder et al, Sequence and structural features of plant and fungal tyrosinases. Phytochemistry. Aug. 1997;45(7):1309-23.*
Galye et al, Identification of regions in interleukin-1 alpha important for activity. J Biol Chem. Oct. 15, 1993; 268(29):22105-11.*
Whisstock et al, Prediction of protein function from protein sequence and structure. Q Rev Biophys. Aug. 2003;36(3):307-40. Review.*
EST database Acc. No. CF871153 Oct. 31, 2003 from Diener et al, FEMS Microbiol Lett 230(2) (2004) 275-282. Alignment with Seq Id No. 4.*
Chang et al, Dissecting Intracellular Signaling Pathways with Membrane-Permeable Peptides Sci. STKE, Aug. 29, 2000 vol. 2000, Issue 47, p. 1-11.*
"Shiitake mushroom tyrosinase enzyme", Dec. 18, 2001, XP002484520, Database accession No. AAG67089.
"Shiitake tyrosinase protein sequence", Sep. 17, 1998, XP002484521, Database accession No. AAW62552.
"Aspergillus oryzae melD protein SeqID1", Oct. 7, 2004, XP002484522, Database accession No. ADQ58743.
"Tobacco polyphenol oxidase partial polypeptide TOBPPO25", Jun. 21, 1999, XP002484523, Database accession No. AAW97991.
"Tobacco polyphenol oxidase GTP01", Mar. 23, 1998, XP002484662, Database accession No. AAW23666.
Selinheimo Emilia et al., "Production and characterization of a secreted, C-terminally processed tyrosinase from the filamentous fungus Trichoderma reesei", Sep. 2006, The Febs Journal Sep. 2006, pp. 4322-4335.
European search report in corresponding EP 06708959.
Halaouli S et al. Characterization of a new tyrosinase from Pycnoporus species with high potential for food technological applications. Journal of Applied Microbiology, Feb. 2005, vol. 98, issue 2, pp. 332-343, the whole document.
Database EMBL [Online] Aug. 16, 2005 Birren B W et al: "Hypothetical protein" retrieved fro EBI, Database accession No. Q4IAY0 50% identity with Seq Id No. 3 in 607 aa overlap (6-602:4-554).
Database EMBL [Online] Aug. 16, 2005 Birren B W et al.: "Hypothetical protein" retrieved from EBI, Database accession No. Q4HZT6 47% identity with Seq Id No. 4 in 560 aa overlap (2-557:15-550).
Score et al "extracellular phenoloxidase and oeroxidase enzyme production during interspesific fungal interactions". Int. Biodeterioration and Biodegradation vol. 39, No. 2-3, 1997. s. 225-233. (tiivistelma, taulukko 1 ja 2, 228).
Mackie et al. "Effects and incidence of volatile organic compound interactions between bacterial and fungal isolates". Soil Biology and Biochemistry. vol. 31, 1999. s. 375-385. (tiivistelma, taulukko 1) .
Obata et al. Cloning of novel tyrosinase-enciding gene (melB) from *Aspergillus oryzae* and its overexpression in solid-state culture (rice koji). Journal of Bioscience vol. 97, No. 6, 2004. s. 400-405.
NCBI/GenBank AN: BAD51402. "Photo-regulated tyrosinase gene in Polyporus arcularius". Morinaga Sep. 17, 2003.
NCBI/GenBank AN AAB07484. "Molecular and functional characterization of the tyrosinase gene of the filamentous fungus Podospora anserina". Marbach et al., Aug. 8, 1996.

* cited by examiner

*Primary Examiner* — Sheridan Swope
(74) *Attorney, Agent, or Firm* — Young & Thompson

(57) ABSTRACT

Extracellular tyrosinases obtainable from *Trichoderma* spp. and methods for producing them by recombinant technology. The enzymes are particularly useful in cross-linking food proteins.

12 Claims, 5 Drawing Sheets

```
TYR1,    1  MGFLARLTWVFHLVLLLVAA..
TYR2,    1  MLLSASLSALALATVSLA--..
            *   * *        *

↓
TYR1,   21  .QDYDFGVDVISITRRRDTDAPIVVGRLPSASNGSTPLRLEIRDVKADKYRWDLYI
TYR2,   19  ..---------------QGTTHIPVTGVPVSPGAAVPLRQNINDLAKSGPQWDLYV
                              *   *       ***    *  *     ****

TYR1,   76  LALSMFQSVNQDDPLSYYQVAGIHGVPFVTWNGVGPAAGASQSGYCPHSSVLFPTWHRPY
TYR2,   58  QAMYNMSKMDSHDPYSFFQIAGIHGAPYIEYNKAGAKSGDGWLGYCPHGEDLFISWHRPY
             *      **  *   *  *****  *    *     *       **** **  *****

TYR1,  136  LALYEQELHKLAGAIADMFANATERFLYRQAASDFRIPYWDWASPAPEGESHFPDVFWNS
TYR2,  118  VLLFEQALVSVAKGIANSYPPSV-RAKYQAAAASLRAPYWDWAADSSVPAVTVPQTLKIN
             * **  *   *    **        *  ** *   * ******     *

TYR1,  196  TMIQYGPNGVQVIRNPLYSYSFHPLDGDALIWPPLRSWNETKRAPNTEISQAEPPSMNDQ
TYR2,  177  VPSGSSTKTVDYT-NPLKTYYF-PRMSLTGSYGEFTGGGNDHTVRCAASKQSYPATAN--
                *       ***  *  *                          *   *   *

TYR1,  256  VSAALLARLPEIQQRLYILFSSYHEFDSFSNK-NYA-FSQNLSHLDSIEAVHDIIHIYGG
TYR2,  233  --SNLAAR-PYKSWILVTDTESGPQYDVLTNSQNFADFASTSGPGINVEQIHNAIH-WDG
              * ** *      *       *      *    *  *          ** **  *

TYR1,  314  SRGHMTYVP-LSSFDPLRFLHHAMTDRLISMWQLLNPSAWM-TPQISGETTYTALKGTMQ
TYR2,  289  ACGSQFLAPDYSGFDPLFFMHHAQVDRMWAFWEAIMPSSPLFTASYKGQSRFNSKSGSTI
             *       *  ****** ** **  **      **         *     *       *

TYR1,  372  NSSTPLTPFMSSADGTFWDSDMSRSTEVFGYAYGDTSYVPGDSESPRNKLIRKINRWLGL
TYR2,  349  TPDSPLQPFYQ-ANGKFHTSNTVKSIQGMGYSYQGIEYWQKSQAQIKSSVTTIINQLYGP
             *  **  **    *  *    * *     **  *     *        *      *

TYR1,  432  NSP (SEQ ID NO: 9)
TYR2,  408  NSG (SEQ ID NO: 10)
            **
```

PROTEINS HAVING TYROSINASE ACTIVITY

FIELD OF THE INVENTION

The present invention relates to enzyme technology, and more precisely to novel fungal enzyme proteins and their uses. It further relates to polynucleotides encoding the enzymes, methods of producing them, and to expression vectors and host cells useful in the production of the enzymes.

BACKGROUND OF THE INVENTION

Enzymes are used in various types of industrial processes in the pulp and paper industry, textile industry, and in the food, feed and beverage industry. Enzymes are also used in the cosmetic and pharmaceutical industry and in detergents. The industrial enzymes can be of animal, plant or microbial origin, and extracellular enzymes are preferred. They are usually more stable and can easily be produced by recombinant technology. The isolation and purification of intracellular enzymes from the host cells is costly and laborious, and therefore it is an advantage, if the enzyme is extracellular i.e. a protein that is secreted from the cell. Further it is desirable that the enzyme can be produced in great amounts in an industrial scale and that the organism is safe, and easy and economic to cultivate.

Proteins are significant constituents in renewable raw materials and thus food, textile fibres etc contain significant amounts of protein. Enzymes can be used for modification of the proteins and their technological properties in these materials. Protein matrix can be modified by hydrolytic enzymes (proteases) being able to decrease the molecular weight of the protein. Proteins can also be modified by enzymes being able to create covalent cross-links between amino acid residues in proteins (as an example transglutaminase, which creates isopeptide links between lysine and glutamine residues) or by enzymes being able to oxidize certain amino acid residues. Oxidation of certain amino acid residues can in turn also result in formation of cross-links. Modification of proteinaceous material by cross-linking is frequently used e.g. in food processing. Regarding food quality, texture is a very essential factor. It is not only related to sensory perception but also to water holding capacity, gelling and emulsifying properties and stability.

Enzyme-aided structure engineering via protein cross-linking can be exploited in several food applications, e.g. in meat, fish, dairy and cereal processing. Transglutaminase is a well known enzyme e.g. for cold-binding of meat parts together to produce restructured meat products, for texture improvement and water holding capacity of minced meat products, improvement of structure of fish raw materials, milk gel forming in yoghurt production with better water holding without undesirable syneresis effect, prevention of texture deterioration of pasta products after cooking, improved loaf volume of bread baked from low-grade flours. Enzymatic cross-linking of vegetarian foodstuff with e.g. transglutaminase is disclosed in WO 03/007728.

Transglutaminase is known to catalyse cross-linking in or between proteins via formation of ε(γ-glutamyl) lysine isopeptide bonds in/between different proteins such as myosin, gelatine and collagen, casein, caseinate, whey protein, soy protein, gluten, egg proteins (Kuraishi et al., 2001; Nielsen, 1995). The reactivity is, however, dependent on the availability and accessibility of the target amino acids, i.e. lysine and glutamine in the protein substrate. Thus, not all proteins are suitable substrates for transglutaminase due to insufficient accessibility or limited quantity of glutamine or lysine residues in the protein.

Phenol oxidases using oxygen as an electron acceptor are particularly suitable for enzymatic processes as no separate cofactors needing expensive regeneration i.e. NAD(P)H/NAD(P) are required in the reactions. These phenol oxidases include e.g. laccase and tyrosinase. They are both copper proteins and can oxidize various phenolic compounds. The substrate specificity of laccases and tyrosinases is partially overlapping.

Tyrosinase catalyses both the o-hydroxylation of monophenols and aromatic amines and the oxidation of o-diphenols to o-quinones or o-aminophenols to o-quinoneimines (Lerch, 1981). Traditionally tyrosinases can be distinguished from laccases on the basis of substrate specificity and sensitivity to inhibitors. However, the differentiation is nowadays based on structural features. Structurally the major difference between tyrosinases and laccases is that tyrosinase has a binuclear copper site with two type III coppers in its active site, meanwhile laccase has altogether four copper atoms (type I and II coppers, and a pair of type III coppers) in the active site.

Tyrosinase is capable of oxidising tyrosine residues in proteins to the corresponding quinones, which can further react with e.g. free sulfhydryl and/or amino groups resulting in formation of tyrosine-cysteine and tyrosine-lysine cross-links (Ito et al., 1984). Quinones have also been suggested to form tyrosine-tyrosine linkages by coupling together.

Methods for cross-linking proteins by laccases have been disclosed e.g. in US2002/9770. Plant proteins derived from beans and cereals and animal proteins including milk, egg, meat, blood and tendon are listed as suitable substrates. However, laccases form radicals to proteins and also to other possible substrates (e.g. phenolic components). Therefore the process is more difficult to control than quinone-derived non-radical reactions catalyzed by tyrosinase. In the laccase-catalyzed reaction also some stable radicals can retain in the matrix causing depolymerization and subsequent disruption of the matrix as a function of time. Fungal laccases are disclosed in US2002/19038.

The ability of tyrosinase to cross-link food proteins has been reviewed (Matheis and Whitaker, 1984; Matheis and Whitaker, 1987). In these studies intracellular *Agaricus* tyrosinase has been used. The cross-linking of proteins with tyrosinase proceeds via the formation of o-quinones from protein-bound tyrosine. These o-quinones either condense with each other or react with free amino and sulfhydryl groups present in proteins.

Tyrosinases have been suggested for use in cross-linking of whey proteins (Thalmann and Loetzbeyr, 2002) and in modifying the physical properties of dough (Takasaki and Kawakishi, 1997). In addition to food protein applications tyrosinases may be used e.g. in the cosmetic and pharmaceutical field (DE 102 44 124). WO99/57993 discloses the use of cross-linking enzymes in ruminant feed, and US2003/0177589 discloses a method of treating proteinaceous fibres with a tyrosinase enzyme, thereby preventing e.g. shrinkage of wool textiles. Conjugates obtained by contacting a polypeptide such as gelatine and a polysaccharide such as chitosan with a tyrosinase is disclosed in WO2004/029096. The gelatine-chitosan conjugate can be used in medical applications. Tyrosinase has also been used to polymerise tropocollagen macromolecules, which are the constituents of collagen fibres (Dabbous, 1966). Formation of inter- and intramolecular cross-links between tyrosine residues resulted in polymerisation.

Tyrosinases are widely distributed in nature. They are related to melanin and eumelanin synthesis in plants, mammals, and insects. In fruits and vegetables tyrosinase is responsible for enzymatic browning reactions and in mammals for pigmentation. In fungi the role of tyrosinase is correlated with cell differentiation, spore formation, virulence and pathogenesis (Sanchez-Ferrer et al., 1995).

The best known and characterized tyrosinases are of mammal origin. The most extensively investigated fungal tyrosinases both from a structural and functional point of view are from *Agaricus bisporus* (Wichers et al., 1996) and *Neurospora crassa* (Lerch, 1983). Also a few bacterial tyrosinases have been reported, of which *Streptomyces* tyrosinases are the most thoroughly characterized (U.S. Pat. No. 5,801,047 and U.S. Pat. No. 5,814,495). In addition, tyrosinases have been disclosed e.g. from *Bacillus* and *Myrothecium* (EP 919 628), *Mucor* (JP 61115488), *Miriococcum* (JP 60062980) *Aspergillus, Chaetotomastia, Ascovaginospora* (Abdel-Raheem and Shearer, 2002), *Trametes* (Tomsovsky and Homolka, 2004).

Intracellular fungal tyrosinases have been described and they are supposed to be cytoplasmic enzymes (Van Gelder et al., 1997). Indeed the fungal tyrosinase genes analyzed so far do not have a signal sequence, although there are reports claiming that tyrosinase activity has been detected in culture supernatant of some freshwater ascomycetes (Abdel-Raheem and Shearer, 2002), *Chaetomium* (JP 62205783) and *Trametes* spp. (Tomsovsky and Homolka, 2004). The reported tyrosinase activities in culture supernatants can be due to cell autolysis.

Phenol oxidase and peroxidase production during interspecific interactions between two Basidomycetes (*Serpula lacrymans* and *Conidiophora puteana* and several Deuteromycetes (*Trichoderma* spp. and *Scytalium* FY) have been investigated by Score et al., 1997 by preliminary and simple plate analysis. The authors used naphtol and p-cresol as specific substrates for laccases and tyrosinases, respectively. Laccase was detected in the interactions involved in *Serpula lacrymans* and all three *Trichoderma* isolates. Indeed, Hölker et al. 2002 have recently isolated and characterized laccase from *Trichoderma*. Based on results from the preliminary plate tests also tyrosinase activity was suggested in the tested *Trichoderma* species (Score, 1997). However, no tyrosinase was isolated or purified. Mackie et al., 1999 have reported laccase and tyrosinase activity in *Trichoderma viride*, when studying volatile organic compound interactions between soil bacterial and fungal isolates. However, so far tyrosinases have not been isolated nor further characterized from *Trichoderma*.

*Streptomyces* is reported to have an extracellular tyrosinase and secretes the enzyme to culture supernatant, however, the tyrosinase enzyme itself does not have a signal sequence for secretion. The secretion of *Streptomyces* tyrosinase requires a second protein (called MelC1 in *S. antibioticus*) that has a signal sequence (Leu et al., 1992; Tsai and Lee, 1998), and this makes the industrial production of *Streptomyces* tyrosinase more tedious and complicated than production of a naturally secreted tyrosinase.

Microbial tyrosinases have been produced heterologously. Two tyrosinase genes from e.g. *Agaricus bisporus* have been expressed in small amounts in *E. coli* (Wichers et al., 2003). A tyrosinase gene melO from *Aspergillus oryzae* has been produced heterologously in *Saccharomyces cerevisiae* (Fujita et al., 1995). In addition a tyrosinase gene from *Streptomyces antibioticus* was coexpressed in *E. coli* with an ORF438 protein probably involved in protein secretion (Della-Cioppa et al., 1990, U.S. Pat. No. 5,801,047).) However, the expression levels of microbial tyrosinases reported in literature are relatively low, and will not allow high titre production of the enzyme. Indeed the availability of tyrosinase has restricted testing of the enzyme in different applications. In practice the *Agaricus* tyrosinase available from Sigma has been the only commercially available tyrosinase. This commercial enzyme is, however, a crude enzyme with relatively low activity and it is very expensive.

In view of the above, there is still a need for novel tyrosinases that have desirable properties both with respect to activity and availability. For easy recovery, the enzyme should be secreted out of the cell in high amounts, whereby the need for cell disruption is avoided in the isolation process and complications arising from cellular debris can be avoided. The enzyme should further be suitable for production by recombinant technology in commercially acceptable quantities, economically and with minimum environmental and health risks. The use of safe organisms is especially important in food applications. The present invention responds to these demands.

Although intracellular proteins could in principle also be produced in recombinant systems as secreted products by coupling them to a signal sequence, naturally secreted proteins are expected to be much more favourable for extracellular production. This is because they are well adapted to the protein folding and trafficking machineries of the secretory pathway.

SUMMARY OF THE INVENTION

The inventors have identified the first extracellular fungal tyrosinases to our knowledge.

One object of the present invention is to provide said novel enzymes. The enzymes are suitable for use in protein modification.

Another object is to provide methods for protein modification as well as uses of the novel enzymes.

Still another object of the present invention is to provide methods for producing the novel enzymes and means useful in their production.

The present invention now provides novel tyrosinases, which were found in *Trichoderma* fungi. The enzymes are extracellular and well suited for recombinant production and for food protein cross-linking applications. *Trichoderma* is generally known to be an excellent protein producer both homologously and heterologously. Another advantage is that *Trichoderma* is a well-known organism that is generally regarded as safe.

The invention is directed to a protein comprising a segment having tyrosinase activity, wherein said protein comprises an amino acid sequence having at least 70% identity to the amino acid sequence as set forth in SEQ ID NO:3 or SEQ ID NO:4, or to a tyrosinase active fragment thereof. The protein may be obtainable from *Trichoderma* spp. The invention is further directed to an isolated polynucleotide encoding the protein, an expression vector comprising the polynucleotide, and a host cell comprising the expression vector.

The invention is still further directed to a method of producing the novel proteins comprising the steps of: a) inserting into a host cell a polynucleotide encoding said protein, b) growing said host cell under conditions suitable for expression of said protein, and c) optionally recovering and purifying said protein produced.

Alternatively the method of producing the protein, comprises the steps of: inserting into a host cell a promotor effective of enhancing the expression of an extracellular tyrosinase gene, operably linking the promotor to said gene, growing said host cell under conditions suitable for expression of said protein, and optionally recovering and purifying said protein produced.

The invention also includes a protein obtained by any of the methods above.

The invention further includes the use of the protein having tyrosinase activity for modifying protein-containing material, or tyrosine-containing peptides, or for oxidation of tyrosine to L-Dopa. Methods of modifying protein-containing material or tyrosine-containing peptides by contacting them with the protein having tyrosinase activity are provided, as well as a method of oxidising tyrosine to L-Dopa, wherein tyrosine is contacted with the protein having tyrosinase activity.

An enzyme preparation comprising the novel protein, and protein-containing material that has been modified by the protein having tyrosinase activity are also objects of the invention.

Specific embodiments of the invention are set forth in the dependent claims.

Other objects, details and advantages of the present invention will become apparent from the following drawings, detailed description and examples.

BRIEF DESCRIPTION OF THE DRAWINGS

FIG. 1 shows an alignment of the *T. reesei* TYR1 and TYR2 amino acid sequences. The sequences are shown up to the C-terminal cleavage site of TYR2. The signal sequences are on the first row. The putative propeptide cleavage site of TYR1 is shown by an arrow. The amino acid residues involved in formation of the active site structure are shaded. The shaded histidines are ligands for the two Cu atoms in the active site. The thioether bond between cysteine and histidine involved in the active site of the tyrosinases is shown by a horizontal line above the sequence.

DETAILED DESCRIPTION OF THE INVENTION

Figure 2:
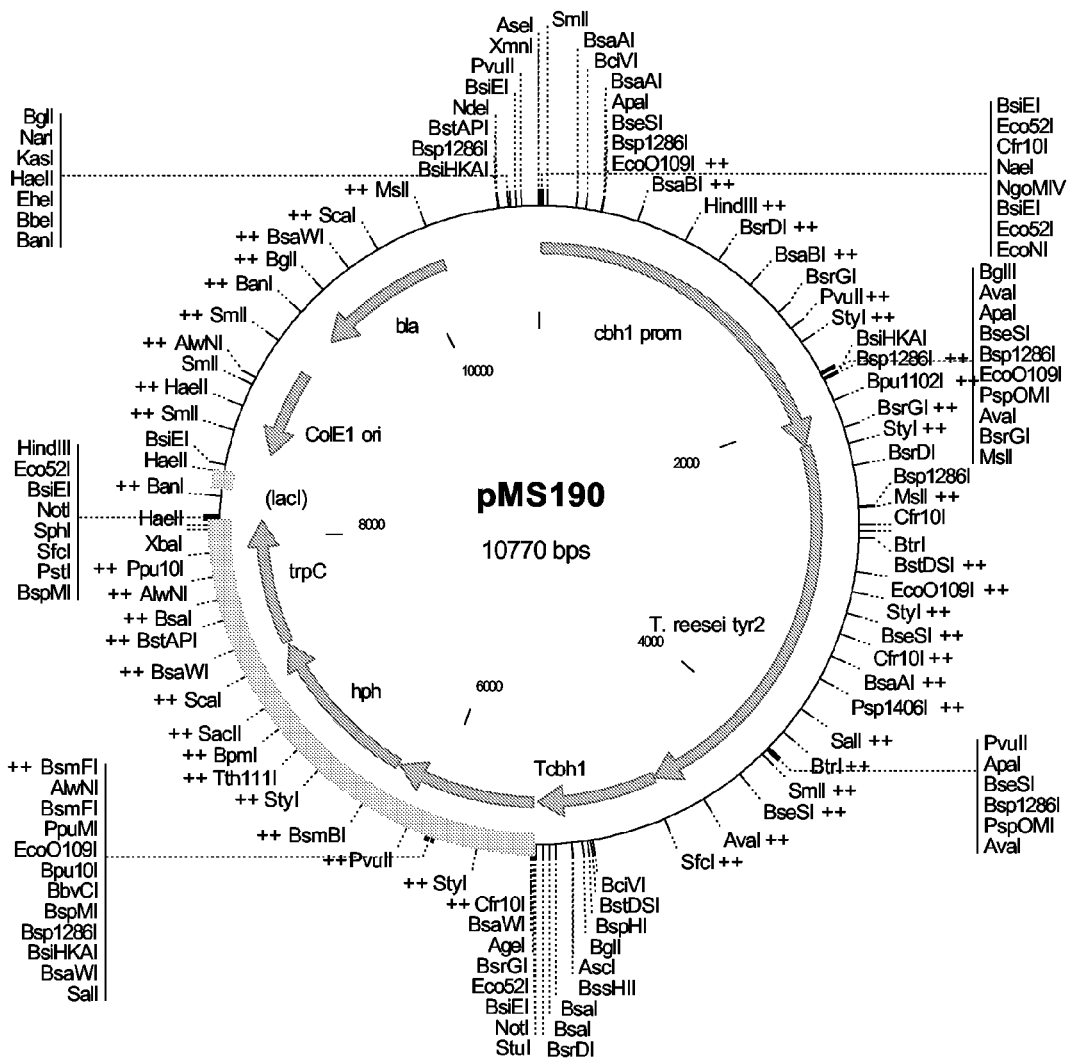
FIG. 2 shows the genetic map of plasmid pMS190 used for transforming a *T. reesei* strain. cbh1 prom, cbh1 promoter; Tcbh1, cbh1 terminator; hph, hygromycin resistance gene; trpC, trpC terminator, ColE1 ori, origin of replication for *E. coli*; bla, beta-lactamase gene.

Tyrosinase is a generally known copper-enzyme. It contains two TIII-type coppers in its active site and it oxidizes various phenolic compounds to the corresponding quinones. The quinones are highly reactive and may react further non-enzymatically. A typical substrate of tyrosinase is tyrosine, which is first hydroxylated into Dopa, which is then further oxidized by the enzyme to dopaquinone. Tyrosinase thus has two enzyme activities in one and the same protein i.e. monophenol monooxyganase activity (EC 1.14.18.1) and catechol oxidase activity (EC 1.10.3.1).

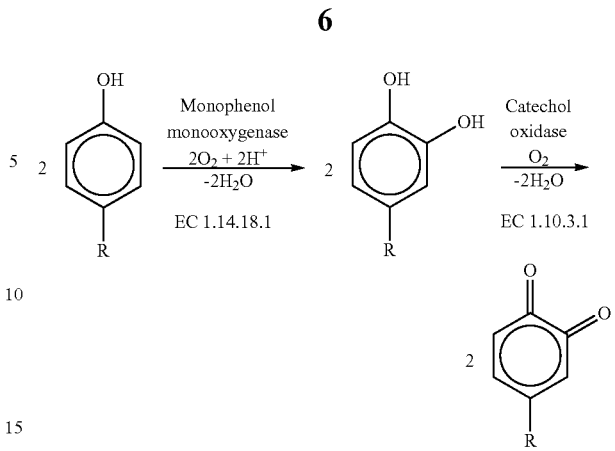

The substrate specificity of tyrosinase is relatively broad, and the enzyme is capable of oxidizing a number of polyphenoles and aromatic amines. Contrary to laccase (EC 1.10.3.2), however, tyrosinase does not oxidize syringaldazin.

The novel proteins are extracellular tyrosinases, which means that they have a signal sequence at their N-terminus, which is cleaved off during secretion. Further processing of the protein during secretion is also possible. In other words the protein is produced intracellularly as an immature protein, which is not necessarily enzymatically active. During secretion the protein is processed into a smaller protein, which is enzymatically active. The processed form of the protein is called the "mature" protein. The protein of the present invention "comprises a segment having tyrosinase activity". This means that the protein may be in the unprocessed form, but that it contains at least that part of the protein that is needed for tyrosinase activity. In other words it contains the mature protein or at least an enzymatically active fragment thereof.

Tyrosinase activity can be measured by techniques generally known in the art. L-Dopa or tyrosine can be used as a substrate, whereafter dopachrome formation may be monitored spectrofotometrically, or alternatively substrate consumption may be monitored by following the oxygen consumption. Tyrosinase activity can also be visualized on agar plates by adding an appropriate substrate such as tyrosine, whereby tyrosinase activity results in a dark zone around the colony.

"Signal sequence" means a sequence of amino acids bound to the N-terminal portion of the protein, which facilitates the secretion of the mature form of the protein outside of the cell. The mature form of the protein lacks the signal sequence.

The novel tyrosinases may be obtainable from *Trichoderma* spp., and encoded by a polynucleotide obtainable from said organism. "Obtainable from" as used herein, means that the proteins or polynucleotides can be obtained from a *Trichoderma* species, but it also includes proteins and polynucleotides similar to those that originate from or are naturally-produced by that particular fungus. Equivalents might especially be found in other filamentous fungi. According to one particular embodiment of the invention the novel proteins are encoded by a polynucleotide obtainable from *Trichoderma reesei*.

The two tyrosinase genes derived from *Trichoderma reesei*, named tyr1 (in scaffold 19) (SEQ ID NO:1) and tyr2 (in scaffold 11) (SEQ ID NO:2) encode proteins of 623 (TYR1) (SEQ ID NO:3) and 571 (TYR2) (SEQ ID NO:4) amino acids. The tyr1 gene comprises three introns at the following nucleotide positions: I 290-355, II 487-571, III 839-890. The tyr2 gene comprises seven introns: I 159-397, II 475-540, III 624-725, IV 774-832, V 1199-1243, VI 1429-

1506, VII 2123-2221. Both TYR1 and TYR2 have a putative signal sequence at the N-terminus, indicating that the enzymes are extracellular. The closest homologues in databases for TYR1 and TYR2 are two different putative tyrosinases from *Gibberella zeae* (47% and 46% identity, respectively). These proteins have been identified in a genome sequencing effort of *G. zeae*, but it has not been shown that they have tyrosinase activity. The two *T. reesei* tyrosinases have 30% identity to each other. An alignment of the amino acid sequences of TYR1 and TYR2 up to the C-terminal cleavage site of TYR2 is shown in FIG. 1. The proteins have a signal sequence in their N-terminus, which means that they are extracellular i.e. they are secreted out of the cells. A signal sequence prediction program suggests that the signal sequence of TYR1 would be 20 amino acids long, and that of TYR2 18 amino acids long.

At least TYR2 is further proteolytically processed at its C-terminus, whereby about ⅓ of the protein is cleaved off. It can be expected that also TYR1 is processed from its C-terminus in a similar way. According to mass spectrometric analysis of the tryptic peptides and of the hydrolysis products of cyanogens bromide treated enzyme, the C-terminal cleavage site of TYR2 is in the amino acid in position 410 (SEQ ID NO: 4), after the sequence -GPNSG. Many fungal tyrosinases are reported to have C-terminal processing. According to literature fungal tyrosinases are activated in vivo by limited proteolytic cleavage which has been suggested to open up substrate access to the catalytic site (Decker and Tuczek, 2000).

In addition, TYR1 may contain a propeptide after the signal sequence at its N-terminal end, which propeptide is cleaved off by a specific kex2-type peptidase during secretion. A possible cleavage site would be between amino acids 36 and 37, after the sequence SITRRR.

TYR1 and TYR2 have two Cu-atoms in their active site. Each of the Cu-atoms is coordinated by three histidine residues. The thioether bond also found in other fungal tyrosinases can be detected between cysteine and the second histidine residue associated with Cu.

The novel proteins are encoded by a polynucleotide that may be obtainable from DNA of *Trichoderma* spp. by amplification with a primer selected from the group consisting of the sequences set forth as SEQ ID NO:5, SEQ ID NO:6, SEQ ID NO:7 and SEQ ID NO:8. Amplification of nucleic acids is generally known in the art. Usually the nucleic acid sequence is amplified by PCR using a primer pair of a forward and a reverse primer that hybridize at each side of the sequence to be amplified. The amplified polynucleotide may have a sequence comprised in SEQ ID NO:1 or SEQ ID NO:2. The novel proteins may have an amino acid sequence comprised in SEQ ID NO:3 or SEQ ID NO:4. "Comprised in" means that the sequence has at least part of the sequence mentioned. Thus the proteins may comprise only a tyrosinase active fragment of SEQ ID NO:3 or SEQ ID NO:4.

Addition, substitution, deletion or insertion of one or more amino acids at one or more sites in the amino acid sequences set forth as SEQ ID NO:3 and SEQ ID NO:4 does not necessarily affect the secretion, processing or enzymatic properties of the proteins. The proteins of the invention may therefore have at least 70%, or at least 80%, and especially at least 90% or at least 95% identity to the amino acid sequence as set forth in SEQ ID NO:3 or SEQ ID NO:4, or to a tyrosinase active fragment of said sequences.

According to one embodiment of the invention, the protein is encoded by a polynucleotide being capable of hybridizing to the nucleic acid having the sequence as shown in SEQ ID NO:1 or SEQ ID NO:2. This includes sequences that hybridize with only part of the identified sequences. Of course it also includes sequences hybridising with any one of the complementary strands. "Hybridizing" refers to the process by which separated nucleic acid strands join with complementary strands by base pairing. The hybridizing conditions are normally of intermediate or high stringency. For example, intermediate stringency hybridisation can be performed in a hybridisation mix containing 6×SSC (0.9 M NaCl in 0.09 M sodium citrate, pH 7), 0.5% sodium dodecyl sulfate (SDS), 5×Denhardt's solution and 100 µg/ml of Herring Sperm DNA at 50° C. High stringency hybridisation can be performed for example in the same hybridisation mix at 68° C.

The polynucleotide encoding the novel protein may have a sequence comprised in SEQ ID NO:1 or SEQ ID NO:2, or being capable of hybridising with a sequence comprised in SEQ ID NO:1 or SEQ ID NO:2.

Because the novel enzymes are extracellular, they are particularly useful for production in large scale. Conveniently the tyrosinase is produced by recombinant technology. This denotes the isolation of a fragment comprising the tyrosinase gene by amplification in a PCR reaction (Coen, 2001) or other recombinant DNA methods (Sambrook et al., 1989), insertion of the gene under a strong promoter in an expression vector, transfer of the vector into suitable host cells and cultivation of the host cells in conditions provoking production of the tyrosinase enzyme. Methods for protein production by recombinant technology in different host systems are well known in the art (Gellissen, 2005). Alternatively only the strong promotor is operably linked to the tyrosinase gene on the host's chromosome, whereby the expression of said gene is overexpressed.

"Expression vector" as used herein refers to a DNA construct comprising a polynucleotide encoding the novel proteins. To be capable of directing the expression of the protein, the vector comprises the following operably linked elements: a transcriptional promotor, the segment encoding said protein, and a transcriptional terminator. The vector can be one that is integrated into the chromosome or an autonomously replicating one.

"Host cell" means any host comprising the expression vector and being capable of expressing the protein encoded by the vector. The host cell may be procaryotic or eucaryotic. Possible hosts are bacteria, yeast and fungi, and especially filamentous fungi. According to one preferred embodiment the tyrosinase is expressed homologously i.e. in *Trichoderma*, and especially in *T. reesei*. Other possible hosts may be *Aspergillus niger, Aspergillus oryzae, Fusarium graminearum, Pycnoporus cinnabarinus, Pichia pastoris, Hansenula polymorpha, Yarrowia lipolytica, Saccharomyces cerevisiae, Escherichia coli* and *Bacillus subtilis*.

A suitable promotor is one having a strong transcription activity and enabling high expression of the tyrosinase. A suitable strong promotor for expression in *Trichoderma* is cbh1, and alternative promotors are for example cbh2, egl1, xyn1, xyn2, and tki1, and the promoter of *Aspergillus nidulans* gpdA.

According to one specific embodiment of the invention the protein is produced by inserting into a host cell a DNA sequence encoding extracellular tyrosinase, which DNA sequence may be obtainable from *Trichoderma* DNA by amplification with a primer pair having the sequences set forth as SEQ ID NO:5 and SEQ ID NO:6, or SEQ ID NO:7 and SEQ ID NO:8, growing said host cell under conditions suitable for expression, and recovering the secreted protein from the growth medium, and optionally purifying it. The protein may be separated from growth medium and further purified from its natural environment by separation and purification techniques known in the art, such as chromatography, precipitation, centrifugation, filtration, gel electrophoresis etc.

The enzyme preparation of the invention is a composition comprising the novel tyrosinase in crude or purified form. In addition it may contain other components including other proteins and enzymes. It may for example be the growth medium of the host cell into which the protein has been secreted.

The *Trichoderma* tyrosinases are useful in formation of quinones to any kind of matrixes comprising phenolic groups reactive therewith subsequent formation of cross-linking as for example in protein matrices.

The *Trichoderma* tyrosinases may be used for treating any protein containing material, and especially proteins that have a relatively high overall-content or relatively high content of accessible tyrosine residues. Also tyrosine-containing peptides can be modified. The enzymes may be applied in different types of industrial applications, such as in the pharmaceutical, cosmetic, pulp and paper, detergent, and textile industry, and in the feed and food industry.

The *Trichoderma* tyrosinases are especially suitable for treating protein-containing food, particularly meat, dairy, vegetable and cereal materials. By cross-linking food proteins with the tyrosinase the texture and rheological properties of the food product can be improved.

Treatment of e.g. fish, poultry or other meat products with the tyrosinases may enhance in obtaining a product with good texture with decreased quantities of other structure forming agents. The tyrosinases may also be used for gelling, whereby the use of gelatin can be avoided. The tyrosinases may further be used for preventing syneresis i.e. separation of the water phase, which is a problem in a number of milk products, especially if the fat content is low. For example in preparing yoghurt, and especially low calorie yoghurt, the solid and the liquid phase tend to separate during storage. This is disapproved by the consumer, and can be prevented by treating the raw materials in yoghurt with tyrosinase. The tyrosinases may also be applied in bakery processes e.g. for hardening the dough, which is especially desired in making frozen dough products.

The tyrosinases may further be used for producing L-Dopa, which is useful in the treatment of Parkinson's disease, and in the production of melanins, which are ingredients for the cosmetic industry. In addition, the tyrosinases may be used for cross-linking proteinaceous fibres or fibre-derived polymers, such as silk, wool, cashmere, alpaca, or human hair.

The invention is illustrated by the following non-limiting examples. It should be understood, however, that the embodiments given in the description above and in the example are for illustrative purposes only, and that various changes and modifications are possible within the scope of the invention.

Example 1

Plate Screening for Tyrosinase-Positive Micro-Organisms

The indicators for tyrosinase activity screening were selected according to literature. L-Tyrosine, p-cresol, p-coumaric acid, tyramine, 3-hydroxy antranilic acid, and catechin were used in concentrations shown in Table 1. *Trichoderma reesei* was grown on Malt Extract agar containing the selected indicators (Table 1) (Difco) at 37° C. for 48 days. Possible colour changes on the plates were observed visually.

*T. reesei* showed clear positive reactions with L-tyrosine, tyramine, 3-hydroxy antranilic acid, and catechin. The results clearly indicated that *T. reesei* was a tyrosinase-positive microbe.

TABLE 1

Plate test screening for tyrosinase activity from *T. reesei*

| Indicator | Concentration (mM) | Colour change |
| --- | --- | --- |
| L-Tyrosine | 10 | ++ |
| p-Cresol | 0.1 | − |
| p-Coumaric acid | 1.0 | − |
| Tyramine | 1.0 | + |
| 3-Hydroxy antranilic acid | 1.0 | + |
| Catechin | 1.0 | ++ |

Example 2

Isolation of tyr1 and tyr2 Genes from *Trichoderma reesei*

Both of the novel tyrosinase genes were amplified by PCR from genomic *T. reesei* DNA. The primers used for tyr1 were forward:

```
                                           (SEQ ID NO:5)
   GCT ACC GCG GAT GGG CTT CCT CGC TCG CCT CAC
``` and reverse:

```
                                           (SEQ ID NO:6)
CTG AGG ATC CTC AGT GGT GGT GGT GGT GGT GCT CCC
ACA ACA CCA ATC TCA GCA T.
```

The tyr2 gene was amplified with the forward primer:

```
                                           (SEQ ID NO:7)
GGG GAC AAG TTT GTA CAA AAA AGC AGG CTA TCA TGC
TGT TGT CAG GTC CCT CTC G
``` and reverse primer:

```
                                           (SEQ ID NO:8)
GGG GAC CAC TTT GTA CAA GAA AGC TGG GTC AGT GGT
GGT GGT GGT GCA GAG GAG GGA TAT GGG GAA CGG
CAA A.
```

The PCR reaction was done with the Dynazyme EXT thermostable polymerase (Finnzymes, Finland) in a reaction mixture recommended by the manufacturer. The PCR program had an initial denaturation step of 3 minutes at 94° C., followed by 25 cycles of 30 seconds at 94° C., 45 seconds at 52° C. and 2.5 minutes at 72° C. This was followed by a final elongation step of 5 minutes at 72° C. The PCR products of the expected size were obtained, run in an agarose gel with methods known in the art and purified from the gel with a Qiaquick Minelute gel purification kit. The tyr1 gene fragment was cloned into the pCR2.1TOPO vector with the TOPO-TA Cloning Kit (Invitrogen). The tyr2 gene fragment was transferred into the pDONR221 vector (Invitrogen) with a BP recombination reaction carried out with the Gateway Recombination kit (Invitrogen). The genes were sequenced to exclude PCR mutations.

Example 3

Over-Expression of tyr2 Gene in *Trichoderma reesei* Under a Strong Promoter The tyr2 gene fragment was transferred by a LR recombination reaction from the pDONR221 vector to the *T. reesei* expression vector pMS186. This vector contains the Gateway reading frame cassette C (RfC) inserted between the cbh1 (cellobiohydrolase 1) promoter and terminator. This vector also has a hygromycin resistance cassette for selection of the *T. reesei* transformants. The LR recombination reaction was done with the Gateway Recombination kit (Invitrogen) as instructed by the manufacturer. In this recombination the tyr2 gene fragment was inserted between the cbh1 promoter and terminator, giving rise to the plasmid pMS190 (FIG. 2).

The plasmid pMS190 was transformed into the *T. reesei* strain VTTD-00775 essentially as described (Penttilä et al., 1987) and transformants were selected for hygromycin resistance on plates containing 125 ug/ml of hygromycin B. The transformants were streaked on plates containing selective medium for three successive rounds and tested for tyrosinase activity with a plate assay. The assay plates had *Trichoderma* minimal medium (Penttilä et al., 1987) with 2% lactose as a carbon source, 1% K-phthalate as a buffering agent (pH5.5), 0.1 mM $CuSO_4$ and 1% tyrosine as an indicator substrate. The transformants were streaked on the plates and grown for 7 days. Tyrosinase activity was observed on the plates as dark brown colour appearing around the streaks. Several positive transformants showing clear staining were found. The parental strain did not show staining in this assay.

Example 4

Production of TYR2 in Liquid Cultures

The positive transformants were grown in shake flasks for 8 days in a *Trichoderma* minimal medium (Penttilä et al., 1987) supplemented with 4% lactose, 2% distiller's spent grain, 100 mM PIPPS and 2 mM $CuSO_4$. Tyrosinase activity was measured from supernatant samples of the cultivations using 15 mM L-Dopa (L-3,4 dihydroxyphenylalanine), (Sigma) as substrate. The activity was also measured on L-tyrosine (Sigma) in concentration of 2 mM. Both activity assays were carried out in 0.1 M sodium phosphate buffer (pH 7.0) at 25° C. monitoring dopachrome formation at 475 nm. The molar extinction coefficient $\epsilon$ 3400 $M^{-1}$ $cm^{-1}$ (Robb, 1984) was used. Measurements were carried out by using a two-beam spectrophotometer (Lambda 20, Perkin-Elmer, Überlingen, Germany). Activities were expressed as nanokatals. The three best transformants produced 40, 35 and 11 nkat/ml of tyrosinase activity.

The transformant pMS190/VTTD-00775/98 producing the highest level of tyrosinase in shake flasks was cultivated in a Braun Biostat C-DCU 3 fermenter (B. Braun Biotech, Germany) in 20 liters of a medium containing (g $l^{-1}$): lactose 20, distiller's spent grain 10, $KH_2PO_4$ 15, and 2 mM $CuSO_4 \times 5$ $H_2O$, pH was adjusted to 5.5-6 with $NH_4OH$ and $H_3PO_4$, and the cultivation temperature was +28° C. Dissolved oxygen level was kept above 30% with agitation 450 rpm, aeration 8 liters $min^{-1}$ and 0-30% $O_2$-enrichment of incoming air. Foaming was controlled by automatic addition of Struktol J633 polyoleate antifoam agent (Schill & Seilacher, Germany). Samples were taken daily to measure lactose and total protein concentration and tyrosinase activity. After fermentation cells were removed by centrifugation and the culture supernatant was concentrated 2.5× with ultrafiltration.

The level of about 300 nkat/ml was reached after six days of cultivation. According to calculation made with the specific activity of the purified TYR2, the highest activity in the fermentation corresponded to about 1 g/L of the enzyme.

Example 5

Purification of TYR2

Centrifuged concentrated culture supernatant (obtained in Example 4) was first treated with Avicel microcrystalline cellulose (0.2 g/ml culture supernatant) to bind and remove cellulases. The sample was incubated at +4° C. for 10 min under constant stirring. Supernatant was collected by centrifugation (10 000 rpm). Buffer was changed to 10 mM Tris-HCl buffer, pH 7.3, with Sephadex G-25 Coarse column (2.6×27 cm; Pharmacia Biotech, Uppsala, Sweden). The subsequent purification steps were carried out with ÄKTA™ purifier (Amersham Biosciences, Uppsala, Sweden). The sample was applied to a HiPrep™ 16/10 CM Sepharose Fast Flow column, which was first pre-equilibrated with 10 mM Tris-HCl buffer, pH 7.3. Proteins were eluted with a linear 0-180 mM NaCl gradient (120 ml) in Tris-HCl buffer. Tyrosinase positive fractions were pooled, concentrated with a Vivaspin 20 (10 000 MWCO, PES, Vivascience) concentrator to 8.2 ml, and applied to a gel filtration column, HiPrep 26/60 Sephacryl S-100 HR column (ÄKTA, Pharmasia) equilibrated with 20 mM Tris-HCl containing 150 mM NaCl, pH 7.5. Active fractions were pooled and concentrated.

SDS-PAGE (12% Tris-HCl Ready Gel, Bio-Rad) was performed according to Laemmli (1970). Protein bands were visualized by staining with Coomassie Brilliant Blue (R350; Pharmacia) and compared with molecular weight markers (Pre-stained SDS-PAGE Standards Broad Range Cat. no. 161-0318, Bio-Rad).

TYR2 appeared as a double band on the PAGE. When further analyzed with gel filtration and reverse phase chromatography, it was observed that only one protein species was present in the purified prep, therefore the double band on the gel is a gel artefact. Interestingly, the molecular weigh of the purified TYR2 as approximated from the gel was only 45 kDa, which is far below the value calculated from the deduced amino acid sequence (60.4 kDa). The result indicated that TYR2 was processed in its C-terminal end.

The purification table is shown in Table 2. Gel filtration 1 and 2 in the Table refer to different pooling of the tyrosinase-positive samples.

TABLE 2

| | Purification of TYR2 | | | | | |
|---|---|---|---|---|---|---|
| Purification step | Activity (nkat/ml) | Protein (mg/ml) | Volume (ml) | Spesific activity (nkat/ml) | Activity yield (%) | Purification factor |
| Culture filtrate | 769.9 | 23.4 | 60 | 33 | 100 | 1.0 |
| Avicel treatment | 719.6 | 17.1 | 44 | 42 | 68.5 | 1.3 |
| Desalting | 389.1 | 12.7 | 63 | 31 | 53.1 | 0.9 |

TABLE 2-continued

Purification of TYR2

| Purification step | Activity (nkat/ml) | Protein (mg/ml) | Volume (ml) | Spesific activity (nkat/ml) | Activity yield (%) | Purification factor |
|---|---|---|---|---|---|---|
| Cation exchange chromatography | 1285 | 4.73 | 8.2 | 272 | 22.8 | 8.3 |
| Gel filtration (1) | 369 | 2.16 | 5.5 | 171 | 4.4 | 5.2 |
| Gel filtration (2) | 238 | 0.61 | 4.4 | 390 | 2.3 | 11.9 |

Example 6

Biochemical Characterization of TYR2

Protein concentration was determined by the Bio-Rad DC protein assay kit (Bio-Rad, Richmond, USA) with bovine serum albumin as standard. Some of the protein concentration determinations were made by monitoring absorbance at 280 nm with a Hitachi U-2000 spectrophotometer (Hitachi, Tokyo, Japan). Tyrosinase activity was measured as described in Example 4.

TYR2 was able to oxidize both L-tyrosine and L-Dopa. The activity readings indicated that L-Dopa gave approximately six times higher activity values than L-tyrosine. The result was also confirmed by determining the enzyme activity on L-Dopa and L-tyrosine by following oxygen consumption in enzymatic reaction. According to literature many microbial tyrosinases require SDS for their activity. The effect of SDS (Sigma) on tyrosinase activity was measured using different concentrations of SDS in the activity assay. Surprisingly, SDS was found to inhibit the enzyme activity: in 0.5 mM SDS concentration the enzymes had only 50% of its activity left.

The isoelectric point (pI) of the enzyme from culture supernatant and purified enzyme was determined by isoelectric focusing within a pH range of 3.5-9.5 (Ampholine PAGplate 3.5-9.5 for IEF, Amersham Bioscience) on an LKB 2117 Multiphor II Electrophoresis System (LKB Pharmacia, Bromma, Sweden) according to manufacturer's instructions. Bands containing tyrosinase activity were visualized by staining the gel with 15 mM L-Dopa in 0.1 M sodium phosphate buffer (pH 7.0) and proteins by Coomassie Blue staining. Purified TYR2 showed two bands at pH ~9, when stained with Coomassie Blue. Under native conditions in isoelectric focusing both the culture filtrate and the purified tyrosinase didn't show a clear band, when stained with L-Dopa, instead the activity was observed as a brown zone at about pH 9.

pH optimum for the tyrosinase was studied by oxygen consumption measurements. Measurements were performed with a single channel oxygen meter (Precision sensing GmbH, Germany) containing fiber-optic oxygen minisensors with measurement range 0-100% oxygen. L-Dopa in 15 mM concentration, dissolved in 0.1 M sodium phosphate buffer, pH 7.0, was used as substrate. Reactions were carried out with 1.8 ml substrate solution and with 4.3 µg of the purified $T.$ $reesei$ tyrosinase. Three different buffers were used according to their buffer capacity. McIlvaine buffer was used within a pH range of 2-7, Tris-HCl buffer (50 mM) within a pH range 7-9 and borate buffer (12.5 mM) within a pH range of 8-9.5. The pH optimum of TYR2 is at 8-8.5. The enzyme has relatively high activity within a quite wide pH range, 5-9. When using Tris-HCl buffer, auto-oxidation of L-Dopa was observed in pH values 8-9, whereas with borate the same kind of phenomenon was not seen. In the measurements with Tris-HCl buffer in pH 8, 8.5 and 9.0 also a blank test without enzyme addition was performed to correct the effect of auto-oxidation in results. The pH optimum of the tyrosinase seemed to be dependant on the buffer.

Figure 3:
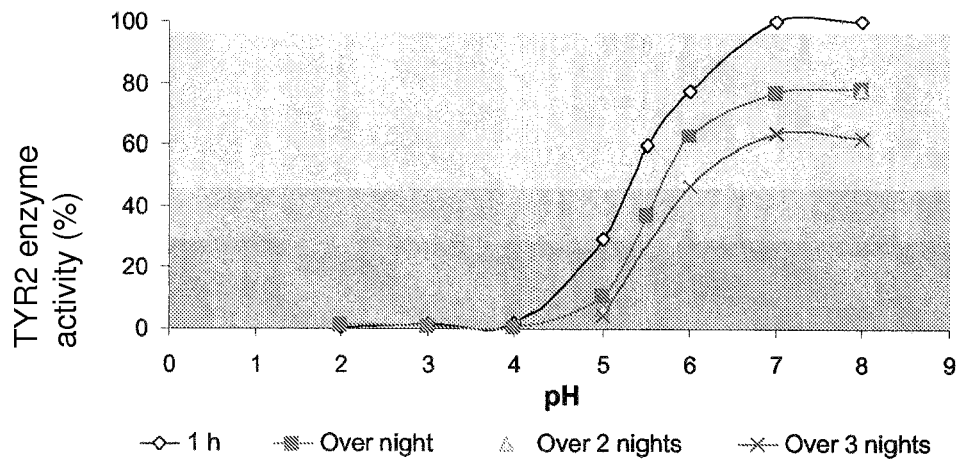
FIG. 3 shows the stability of purified TYR2 within a pH range of 2-8 after 1 h, and 1-3 days.

The stability of the enzyme at different pH-values was determined in McIlvaine, 50 mM $Na_2HPO_4$-25 mM citric acid, buffer by incubating the enzyme solution in different pH-values at room temperature. The residual tyrosinase activity was determined by measuring the activity of the enzyme solutions with L-Dopa as substrate. The results are shown in FIG. 3.

Figure 4:
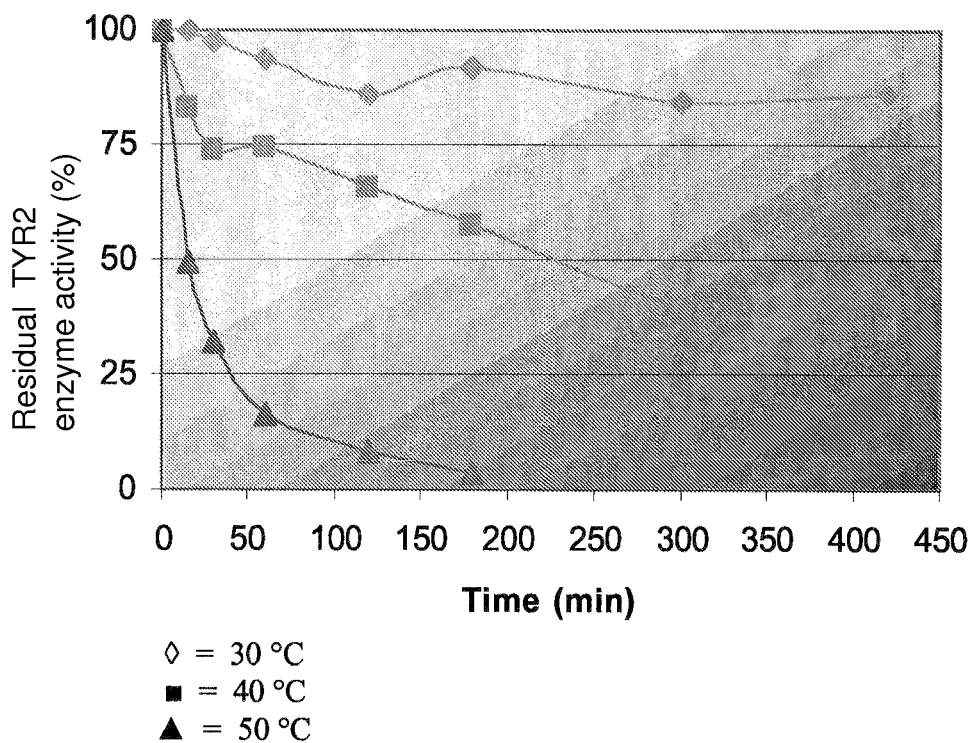
FIG. 4 shows thermal stability of purified TYR2 determined at 30°, 40° C. and 50° C.

Temperature stability was determined at 30, 40 and 50° C. The enzyme solution (320 nkat/ml) in 20 mM Tris-HCl buffer (pH 7.5) was incubated in different temperatures and the residual enzyme activity was determined after certain time periods measuring the tyrosinase activity with the standard activity assay on 15 mM L-Dopa. The results are shown in FIG. 4. The enzyme showed good stability at neutral and alkaline pH. When pH was dropped under 7, the enzyme started to loose activity.

The molecular mass of the tyrosinase and N-terminal sequencing were determined by MALDI-TOF mass spectrometry on a Ultraflex™ time-of-flight instrument (Bruker-Daltonics, Germany) as previously described (Palonen et al. 2003). The molecular mass of the tyrosinase as analyzed by MALDI-TOF was about 42.9 kDa. The N-terminal amino acid analysis indicated that N-terminus was blocked. This refers to the presence of glutamine as the first amino acid in the mature protein. The result is compatible with the sequence data.

The optical absorption spectrum of purified TYR2 was measured with a Varian Cary 100 Bio UV-visible spectrophotometer. The ultraviolet-visible absorption spectrum of the purified tyrosinase had a major protein peak at 280 nm, with a shoulder at 330 nm. The shoulder is an indication of a T3 type copper pair in its oxidized form with bridging hydroxyl.

Example 7

Substrate Specificity of the Tyrosinase

Substrate specificity of the tyrosinase on various selected substrates was studied by oxygen consumption measurements. The concentration of substrates was 2.5 mM, and the compounds were dissolved in 0.1 M sodium phosphate buffer, pH 7.0. Reactions were carried out with 1.8 ml of 2.5 mM substrate solutions and with 24 µg of the purified TYR2. As a reference the substrate specificity assays were also determined for the commercial $Agaricus\ bisporus$ crude tyrosinase (Sigma). Respectively, 50 µg of said mushroom tyrosinase was used in the assays. The structures of the mono-, di- and tri-phenolic compounds used in the study are shown in Table 3 and 4. Activity of TYR2 and $Agaricus$ tyrosinase were analyzed on selected model peptides containing tyrosine in different positions in the peptide chain (Table 5). Oxidation of L-/DL-D-Dopa and -tyrosine by TYR2 and $Agaricus$ tyrosinase was also measured (Table 6).

TABLE 3

*Activity of T. reesei and Agaricus tyrosinase in relation to L-tyrosine (%) with mono-phenolic compounds. Oxygen consumption is based on the linear part of the O2 consumption curve*

| SUBSTRATE (mono-phenols) | TYR2 Relative oxygen consumption (%) | Agaricus tyr Relative oxygen consumption (%) | Structure |
| --- | --- | --- | --- |
| L-Tyrosine | 100 | 100 | 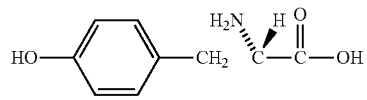 |
| Phenol | 121 | 85 | 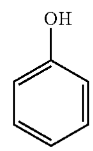 |
| 4-Mercaptophenol | 0 | 0 | 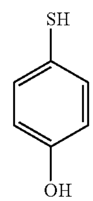 |
| p-Cresol | 172 | 104 | 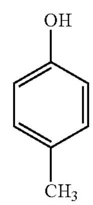 |
| 4-Aminophenol | 8 | 9 | 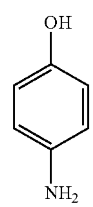 |
| 3-Hydroxyanthranilic acid | 0 | 0 | 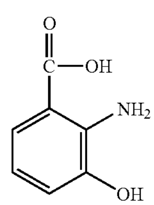 |
| Tyramine | 42 | 85 | 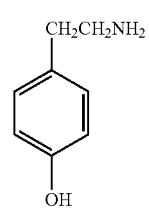 |

TABLE 3-continued

Activity of *T. reesei* and *Agaricus* tyrosinase in relation to L-tyrosine (%) with mono-phenolic compounds. Oxygen consumption is based on the linear part of the O2 consumption curve

| SUBSTRATE (mono-phenols) | TYR2 Relative oxygen consumption (%) | *Agaricus* tyr Relative oxygen consumption (%) | Structure |
|---|---|---|---|
| p-Tyrosol | 346 | 157 | 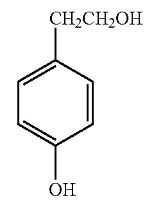 |
| p-Coumaric acid | 390 | 0 | 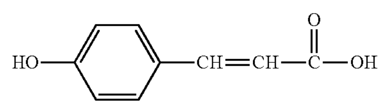 |
| o-Coumaric acid | 0 | 0 | 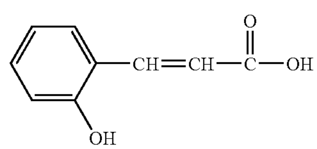 |
| Ferulic acid | 0 | 0 | 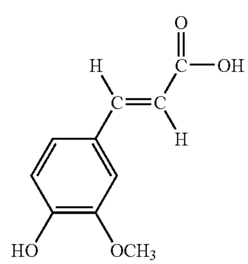 |

TABLE 4

Activity of *T. reesei* and *Agaricus* tyrosinase in relation to L-Dopa (%) with di- and tri-phenolic compounds. Oxygen consumption is based on the linear part of the O2 consumption curve

| Substrate | TYR2 Relative oxygen consumption (%) | *Agaricus* tyrosinase Relative oxygen consumption (%) | Structure |
|---|---|---|---|
| DI-PHENOLS | | | |
| L-Dopa | 100 | 100 | 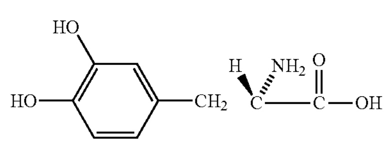 |
| (−)-Epicatechin | 106 | 286 | 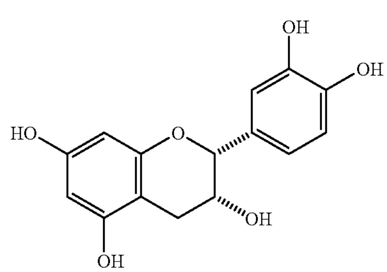 |

TABLE 4-continued

Activity of *T. reesei* and *Agaricus* tyrosinase in relation to L-Dopa (%) with di- and tri-phenolic compounds. Oxygen consumption is based on the linear part of the O2 consumption curve

| Substrate | TYR2 Relative oxygen consumption (%) | *Agaricus* tyrosinase Relative oxygen consumption (%) | Structure |
|---|---|---|---|
| (+)-Catechin hydrate | 220 | 282 | 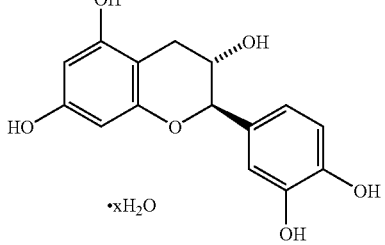 |
| Pyrocatechol | 88 | 328 | 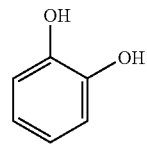 |
| TRI-PHENOLS | | | |
| Pyrogallol | 55 | 248 | 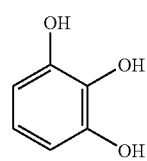 |

TABLE 5

Activity of *T. reesei* and *Agaricus* tyrosinase in relation to L-tyrosine (%) on di-peptides. Oxygen consumption is based on the linear part of the O2 consumption curve

| Substrate ** | TYR2 Relative oxygen consumption (%) | *Agaricus* tyrosinase Relative oxygen consumption (%) |
|---|---|---|
| Y | 100 | 100 |
| DI-PEPTIDES | | |
| YG | 128 | 140 |
| GY | 292 | 115 |

**Y = tyrosine and G = glycine

TABLE 6

Oxidation of L-/DL-D-dopa and -tyrosine by *T. reesei* and *Agaricus* tyrosinase

| Substrate | TYR2 Relative oxygen consumption (%) | +/− (%) | *Agaricus* tyrosinase Relative oxygen consumption (%) |
|---|---|---|---|
| L-dopa | 100 | | 100 |
| DL-dopa | 46 | 2 | 118 |
| D-dopa | 18 | 1 | 106 |
| L-tyrosine | 100 | | 100 |
| DL-tyrosine | 40 | 3 | 102 |
| D-tyrosine | 7 | 1 | 61 |

TYR2 was able to oxidize many substituted monophenols, which had the OH-group in the para-position. Any side chain in ortho-position to the phenolic hydroxyl group caused sterical hindrance, resulting in lower or non-existing oxidation of the substrate. The presence and the position of an amine group in the substrate structure appeared to be essential considering the rate of oxygen consumption by TYR2. The closer the phenol's hydroxyl group to the amino group was, the slower was the oxidation of the substrate. The same influence of the position of amino group was also seen in peptide measurements. Interestingly, the substrate specificity of TYR2 substantially differed from the substrate specificity of *Agaricus* tyrosinase. TYR2 is stereospecific compared to *Agaricus* tyrosinase.

As can be seen from Table 5 TYR2 and *Agaricus* tyrosinase were able to oxidize the tested model peptides. Oxidation rate of TYR2 was very much dependent on the length of the peptide and the position of a tyrosine residue. The di-peptides were oxidized more readily than single tyrosine, and the peptide having tyrosine residue in the C-terminus was a better substrate for TYR2 than the peptide, in which tyrosine was in the N-terminus. *Agaricus* tyrosinase was not sensitive to the position of tyrosine residue.

Surprisingly the *Trichoderma* tyrosinase showed high stereospecificity on L-tyrosine and L-dopa (Table 6). The L-enantiomers were oxidized with much higher rate than the D-enantiomers. With the *Agaricus* tyrosinase no difference in the oxidation rate between different enantiomers was observed. Indeed, Espin et al (1998) have shown that *Agaricus* tyrosinase showed stereospecificity in its affinity towards different enantiomers but not in the reaction rate. The clear difference in reaction rates is an advantage in synthetic chemistry.

The cross-linking ability in model proteins of TYR2 was also analyzed by following changes in MW on SDS-PAGE. The results indicated that TYR2 was able to cross-link α-casein and chicken myofibril, but not bovine serum albumin. Details are given in examples 8 and 9.

Example 8

Tyrosinase-Catalysed Cross-Linking of Meat Proteins

Changes in the molecular weight of the isolated salt soluble proteins (SSP) of chicken breast muscle myofibrils caused by TYR2 were analysed by SDS-PAGE. SPP were isolated according to Xiong and Brekke, 1989. For enzyme treatment SSP was suspended in 50 mM Na-phosphate buffer, pH 7, containing 0.6 M NaCl to the protein concentration of 3 mg/ml. 120 nkat or 240 nkat of TYR2 per gram of protein was added to the suspension. Control suspension was treated in a similar way but without enzyme addition. Reaction mixture was incubated at 30° C. Samples were drawn at the time points of 2 min, 1 hour, 3 hours and 24 hours. SDS-PAGE sample buffer was added and the samples were heated in a boiling water bath. 20 µg of protein from each sample was loaded onto 12% Tris-HCl polyacryl amide gels. SDS-PAGE was performed according to Laemmli, 1970.

The major changes in the protein bands catalysed by TYR2 were tentatively identified by comparing their relative mobility and staining intensity to those treated similarly but without the enzyme. In the conditions and with the dosages used TYR2 produced the following detectable electrophoretic changes, which are most prominent after 24 h enzyme treatment: (1) progressive disappearance of the myosin band of ~200 kDa with both enzyme dosages after 3 h treatment, (2) progressive disappearance of the band of ~36 kDa with both enzyme dosages after 3 h treatment and (3) appearance of large molecular weight protein products (>200 kDa) which did not enter the gel after 24 h treatment.

Ability of TYR2 to form cross-links in a chicken myofibril matrix was also investigated as a development of storage modulus (G') measuring gel forming ability at low deformation. Measurements were carried out during heating at constant temperature using a Bohlin Rheometer. Chicken breast myofibrils were isolated according to Xiong and Brekke (1989) omitting EDTA and $NaN_3$ from the isolation buffer. Isolated myofibrils were suspended in 50 mM Na-phosphate buffer, pH 6, supplemented with 0.30 M NaCl to the protein concentration of 40 mg/ml. Suspensions were treated with 240 nkat of TYR2 per gram of protein at 25° C., 30° C. and 40° C. for 3 hours. Control samples were treated in a similar way but without enzyme.

Figure 5:
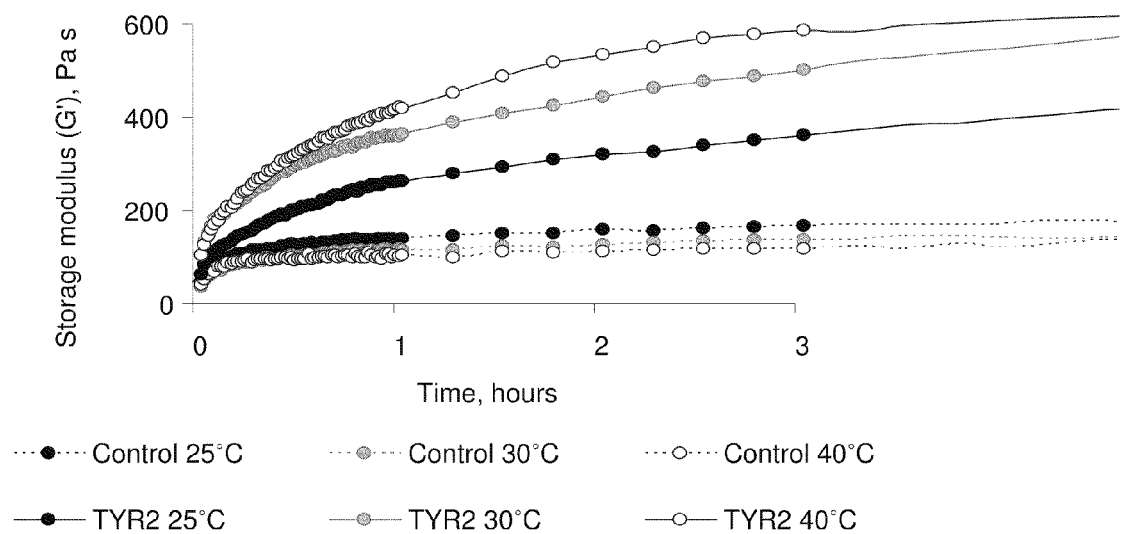
FIG. 5 shows the gel forming efficiency of myofibrillar proteins by TYR2 at 25° C., 30° C. and 40° C.

The results show that the TYR2 treatment of the myofibril samples caused greater increase in G' than those treated only in Na-phosphate buffer. (See FIG. 5; The lines from the bottom to the top indicate: Control 40° C., control 30° C., control 25° C., TYR2 25° C., TYR2 30° C. and TYR2 40° C.) The increase of the treatment temperature intensified gel forming. Thus cross-links were formed to chicken myofibril protein matrix by TYR2.

Example 9

Gelling of Dairy Protein by tyr2

Figure 6:
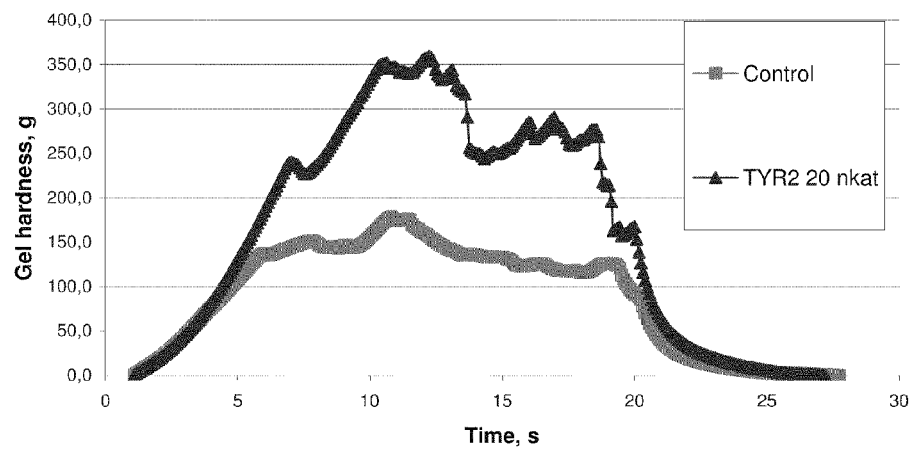
FIG. 6 shows hardness of caseinate gels with and without TYR2 treatment.

3% of commercial caseinate was mixed in water and 0.4% GDL (glucono-delta-lactone) and 20 nkat/g protein of TYR2 was added to the mixture. It was allowed to rest for 22 hours at room temperature, whereafter the gel hardness was measured by Texture Analyzer (FIG. 6). Tyrosinase treatment doubled the hardness of the caseinate gel.

Example 10

Effect of TYR2 on Wheat Dough Characteristics

The influence of TYR2 on the large deformation rheology of wheat dough was investigated by using Kieffer extensibility rig (Stable Micro Systems, Ltd. United Kingdom). Dough extensibility and resistance to extension were measured as a function of enzyme dosage and dough's resting time.

Wheat flour was mixed with Farinograph (Brabender, Germany) using 12 g flour and 7.2 ml liquid phase (60%). Tyrosinase (1 and 10 nkat/g flour) was added to water right before mixing with flour. Mixing time was 4 min. Subsequently, dough was placed into a mould to produce approximately 10-12 test strings. The pressed mould was kept at room temperature for 15-45 min to allow stress relaxation. In the Kieffer tests, dough strings were centrally extended until the elastic limit of the string was exceeded and it ruptured. Maximum resistance $R_{max}$, maximum extensibility $E_{max}$ and extensibility $E_x$ at $R_{max}$ were determined by recording the peak force and the distance at the maximum and at the extension limit. All dough preparations, enzyme treatments and measurements were performed at room temperature, approximately at 22° C.

Figure 7:
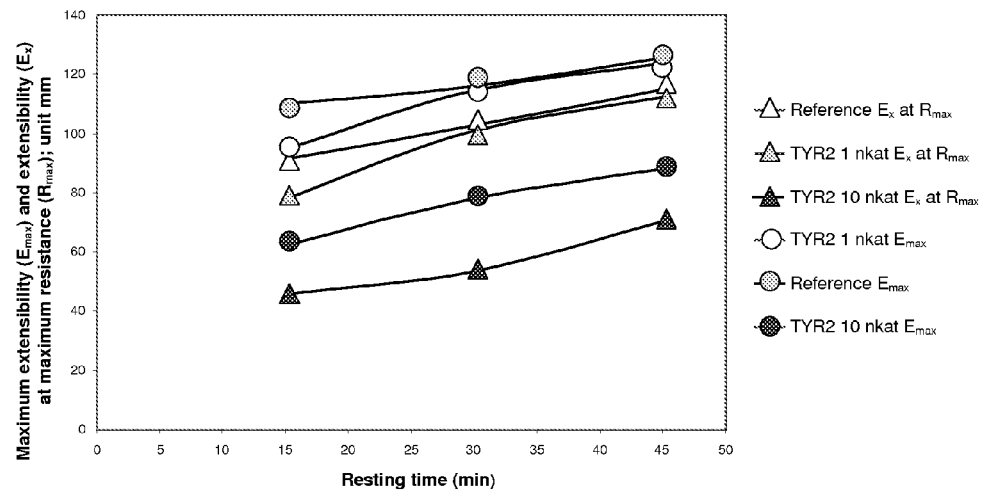
FIG. 7 discloses the effect of TYR2 on the maximum distance $E_{max}$ (mm) and the distance $E_x$ at $R_{max}$ (mm) parameters of wheat dough as a function of resting time.
Figure 8:
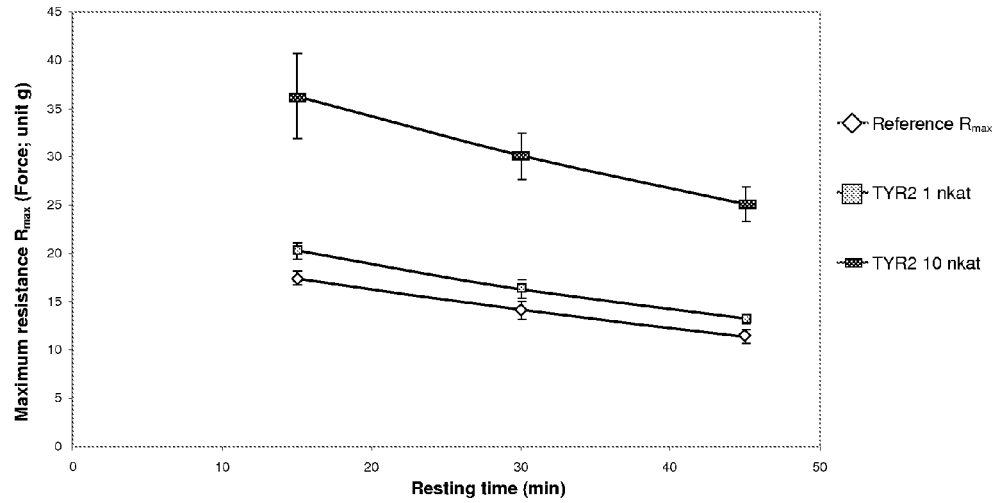
FIG. 8 shows the effect of TYR2 on the force (g) parameter of wheat dough as a function of resting time.

Results from the Kieffer experiments are shown in FIGS. 7 and 8. They show that TYR2 increased the maximum resistance $R_{max}$ of dough and decreased the dough extensibility $E_x$ at $R_{max}$ indicating hardening of dough. Increasing the enzyme dosage intensified the hardening of dough.

REFERENCES

Abdel-Raheem, A., and Shearer, C. A. 2002. Extracellular enzyme production by freshwater ascomycetes. Fungal Diversity 11, 1-19.

Coen, D. M. 2001. The polymerase chain reaction. In: Ausubel, F. M., Brent, R., Kingston, R. E., More, D. D., Seidman, J. G., Smith, K. and Struhl, K. (eds.) Current protocols in molecular biology. John Wiley & Sons. Inc., Hoboken, USA.

Dabbous, M. K. 1966. Inter- and intramolecular cross-linking in tyrosinase-treated tropocollagen. J. Bio. Chem. 241, 5307-5312.

Decker, H. and Tuczek, F. 2000. Tyrosinase/catecholoxidase activity of hemocyanins: structural basis and molecular mechanism, Trends Biochem. Sci. 25, 392-397.

Della-Cioppa, G., Garger, S. J., Sverlow, G. G., Turpen, T. H., and Grill, L. K. 1990. Melanin production in *Escherichia coli* from a cloned tyrosinase gene. Bio/Technology 8, 634-638.

Espin, J. C., Garcia-Ruiz, P. A., Tudela, J., and Garcia-Canovas, F. 1998. Study of stereospecificity in mushroom tyrosinase, Biochem. J. 331, 547-551.

Fujita, Y., Uraga, Y., and Ichisima, E. 1995. Molecular cloning and nucleotide sequence of the protyrosine gene, melO from *Aspergillus oryzae* and expression of the gene in yeast cells. Biochimica Biophysica Acta 1261, 151-154.

Gellissen, G. (ed.) 2005. Production of recombinant proteins. Novel microbial and eukaryotic expression systems. Wiley-VCH Verlag Gmbh&Co. weinheim, Germany.

Hölker, U., Dohse, J., and Höfer, M. 2002. Extracellular laccase in ascomycete *Trichoderma atroviride* and *Trichoderma harzianum*, Folia Microbiol. 47, 423-427.

Ito, S., Kato, T., Shinpo, K, and Fujita, K. 1984. Oxidation of tyrosine residues in proteins by tyrosinase, Biochem. J. 222, 407-411.

Kuraishi, C., Yamazaki, K., and Susa, Y. 2001. Transglutaminase: its utilization in the food industry. Food Rev. Int. 17, 221-246.

Laemmli, U K. 1970. Cleavage of structural proteins during the assembly of the head of bacteriophage T4. Nature 227, 680-685.

Lerch, K. 1981. Copper monooxygenases: Tyrosinase and dopamine γ-hydroxylase. In H. Sigel (Ed.), Metal ions biological systems (pp. 143-186). New York, Marcel Dekker.

Lerch, K. 1983. Neurospora tyrosinase: structural, spectroscopic and catalytic properties, Mol. Cell. Biochem. 52, 125-138.

Leu, W. M., Chen, L. Y. and Lee, Y. H. 1992. Secretion of the Streptomyces tyrosianse is mediated through its trans-activator protein, melC1. J. Biol. Chem. 267, 20108-20113.

Matheis, G. and Whitaker, J. R. 1984. Modification of a protein by polyphenol oxidase and peroxidase and their products, J. Food Biochem., 8, 137-162.

Mackie A. E. and Wheatley R. E. 1999. Effects and incidence of volatile organic compound interactions between soil bacterial and fungal isolates. Soil Biology and Biochemistry 31, 375-385.

Matheis, G. and Whitaker, J. R., 1987. A review: Enzymatic cross-linking of proteins applicable to foods. J. Food Biochem. 11, 309-327.

Nielsen P. M. 1995. Reactions and potential industrial applications of transglutaminase. Review of literature and patents. Food Biotechnology 9, 119-156.

Palonen, H., Saloheimo, M., Viikari, L., and Kruus, K. 2003. Purification, characterization and sequence analysis of a laccase from the ascomycete Mauginiella sp. Enzyme Microb. Technol. 31, 403-410.

Penttilä, M., Nevalainen, H., Rättö, M., Salminen, E., Knowles, J. K. C. 1987. A versatile transformation system for the cellulolytic filamentous fungus Trichoderma reesei. Gene 61, 155-164.

Robb, D. A., Tyrosinase, In Copper Proteins and Copper Enzymes Vol 2, Ed. R. Lontie, CRC Press Inc Boca, Raton, Fla., 1984, 207-240.

Sambrook, J., Fritsch, E. F. and Maniatis, T. 1989. Molecular cloning: A laboratory manual, 2nd edn. Cold Spring Harbor Laboratory, Cold Spring Harbor N.Y.

Sanchez-Ferrer, A., Rodriguez-Lopez, N., Garcia-Canovas, F., Garcia-Carmona F. 1995 Tyrosinase: a comprehensive review of its mechanism, Biochimica et Biophysica Acta 1247, 1-11.

Score, A. J., Palfreyman, J. W., and White, N. A. 1997. Extracellular phenoloxidase and peroxidase enzyme production during interspecidic fungal interactions. Int. Biodeterioration and Biodegradation 39, 225-233.

Takasaki, S. and Kawakishi, S. 1997. Formation of protein-bound 3,4-dihydroxyphenylalanine and 5-S-cysteinyl-3,4-dihydroxyphenylalanine as new cross-linkers in gluten. J. Agr. Food Chem. 45, 3472-3475.

Thalmann, C. R. and Lötzbeyer, T. 2002. Enzymatic cross-linking of proteins with tyrosinase. Eur. Food Res. Technol. 214, 276-281.

Tomsovsky, M., and Homolka, L. 2004. Tyrosinase activity discovered from Trametes spp., World J. Microbiol. Biotechnol. 20, 529-530.

Tsai, T.-Y. and Lee, Y.-H. W., 1998. Roles of copper ligands in the activation and secretion of Streptomyces tyrosinase, J. Biol. Chem. 273, 19243-19250.

Van Gelder, C. W. G., Flurkey, W. H., and Wicjers, H. K. 1997. Sequence and structural features of plant and fungal tyrosinases. Phytochem. 45, 15-21.

Wichers, H. J., Gerritsen, Y. A. M. ja Chapelon, C. G. J., 1996. Tyrosinase isoforms from the fruitbodies of Agaricus bisporus, Phytochemistry 43, 333-337.

Wichers, H. J., Recourt, K., Hendrics, M., Ebbelaar, C. E. M, Biancore, G., Hoeberichts, F. A., Mooibroek, H., and Soler-Rivas, C. 2003. Cloning, expression and characterization of two tyrosinase cDNAs form Agaricus bisporus, Appl. Microbiol. Biotechnol. 61, 336-341.

Xiong, Y. L., and C. J. Brekke, 1989. Changes in protein solubility and gelation properties of chicken myofibrils during storage. J. Food Sci. 54:1141-1146.

---

The invention claimed is:

1. An isolated protein comprising an amino acid sequence having at least 95% identity to residues 19-410 of SEQ ID NO: 4, wherein said amino acid sequence has tyrosinase activity.

2. The isolated protein of claim 1, obtained from *Trichoderma* spp.

3. The isolated protein of claim 1 comprising a signal sequence at the N-terminal end.

4. The isolated protein of claim 1 consisting of amino acids 19-410 of SEQ ID NO: 4.

5. The isolated protein of claim 1, wherein the isolated protein is encoded by a polynucleotide obtainable from DNA of *Trichoderma* spp. by amplification with the primer pair having the sequences set forth in SEQ ID NO:7 and SEQ ID NO:8.

6. The isolated protein of claim 1, wherein the isolated protein is encoded by a polynucleotide obtainable from *Trichoderma reesei*.

7. The isolated protein of claim 1, wherein the isolated protein is encoded by a polynucleotide comprising the sequence as set forth in SEQ ID NO:2.

8. The isolated protein of claim 1 comprising the amino acid sequence as set forth in SEQ ID:4.

9. The isolated protein of claim 1 wherein the amino acid sequence is a tyrosinase active fragment of the amino acid sequence as set forth in SEQ ID NO:4.

10. The isolated protein of claim 1 having a molecular weight of about 42.9 kDa, a pI of about 9, a pH optimum at about 8-8.5, and tyrosinase activity at alkaline or neutral pH.

11. A protein obtained by a method comprising:
  a) inserting into a host cell a DNA sequence encoding an extracellular tyrosinase, wherein said DNA sequence is obtainable from *Trichoderma* spp. DNA by amplification with the primer pair having the sequences as set forth in SEQ ID NO: 7 and SEQ ID NO: 8,
  b) growing said host cell in growth medium under conditions suitable for expression and secretion of the protein, and
  c) recovering the secreted protein from the growth medium, and optionally purifying the protein, wherein the protein comprises an amino acid sequence having at least 95% identity to residues 19-410 of SEQ ID NO: 4, said amino acid sequence having tyrosinase activity.

12. An enzyme preparation comprising the isolated protein of claim 1.

* * * * *

SEQUENCE LISTING

```
<160> NUMBER OF SEQ ID NOS: 10

<210> SEQ ID NO 1
<211> LENGTH: 2075
<212> TYPE: DNA
<213> ORGANISM: Trichoderma reesei
<220> FEATURE:
<221> NAME/KEY: Intron
<222> LOCATION: (290)..(355)
<220> FEATURE:
<221> NAME/KEY: Intron
<222> LOCATION: (487)..(571)
<220> FEATURE:
<221> NAME/KEY: Intron
<222> LOCATION: (839)..(890)

<400> SEQUENCE: 1
atgggcttcc tcgctcgcct cacttgggtc ttccacttgg tccttctttt ggtggccgcc      60
caggactatg actttggcgt cgacgtcatc tccatcactc gtcgacggga taccgacgca     120
cccatcgtcg tcggccgcct gccatcggcc tccaacggga gcacaccccct gagactcgag    180 atccgcgacg tcaaggcaga caaatatcgg tgggacctgt acattctggc gctgagtatg    240
```

```
tttcagtccg tcaatcagga cgatcccctg tcgtattacc aagttgctgg taagtgagat    300
gtgtgaacac gactcggctt tggcctcagc agtctgatga gctttgtgag cctagggata    360
cacggtgtgc cctttgtgac atggaatggg gttggaccag cagcgggagc gagccagtca    420
ggttactgtc cgcatagttc agttctgttt ccaacgtggc accgcccata tctagccttg    480
tacgaggtga gtcggtctgg gttccagaca gccggcgccg gcaacgcccg cacgcacgtt    540
ttgtggacaa gaagatgact ttgctttcca gcaagagctg cacaagcttg ccggtgccat    600
tgccgacatg ttcgccaatg ccactgaacg cttcctctac aggcaagctg cctcggattt    660
tcgtataccg tactgggact gggcatcgcc cgcccctgaa ggcgagagcc attttcccga    720
cgtcttttgg aactcgacca tgatcccaat cggtcccaat ggcgtccaag ttattcgtaa    780
cccgctgtac tcttactcgt tccatccgct tgatggagat gcgctcatct ggccaccggt    840
acgtataatg gagggcaaca tacacacaat cgcctgctga cagctcatag ttgcgaagct    900
ggaacgaaac aaaacgagct ccaaatacag aaatcagtca agccgagcca ccttccatga    960
atgaccaagt gagcgcggcc ttgctggcca gattgcccga gatacagcag cgattgtaca   1020
tactcttctc tagttatcac gagtttgact cgttcagcaa caagaactat gccttttcgc   1080
agaacctcag ccatctggac tctatcgagg ccgttcacga cattatccac atatatggcg   1140
gatctagggg ccatatgacc tatgttcctc tgtcgtcctt tgatccgctc ttcttccttc   1200
accacgccat gacggacagg ctgatatcga tgtggcagct tctcaatccc tcggcatgga   1260
tgactccaca gatctcagga gagacgacat acactgcgct aaagggaacc atgcaaaact   1320
ccagcactcc gcttacgcca ttcatgtcct cagcagacgg cactttctgg gactctgaca   1380
tgtccaggtc aacggaagtg tttggctacg catacggaga cacctcatat gtgcctggcg   1440
actctgagag cccacgcaac aagctgattc gcaagattaa cagatggctt ggcctgaaca   1500
gcccggccat ggttcgaatc aagagccaag cacagaaccg cgacccagc ggcgtatgga   1560 agggcaacac aggcgtcaaa ggcgtccagc ccagcctcaa gatagacatg agcgatgtcg   1620
tggacgacca ttatacggag tggattgcaa atgtacacgt caaccacgga gctttggacg   1680
gatcattcag catttacttc ttcgccggca agccgccagc cgacgtcggc acttgggcgt   1740
ttgctccaaa tctcatggga tcggtcggca tcttcaccat gagcggcatg ggtgccatc   1800 actccaagat gtcgggaagc gtgccgttga ccatggctct gatgaggctg ctagcctag   1860 gagctgtcca aagtgtcgag ccaaactcgg tggtggcgtt tctgcaaagc agactacact   1920
ttcgcatcgc tagcattgat gacaaggaaa ttgacccaag tctcgttgcc gggctcttca   1980
tcgggatcag cagcaccagg gtaaggctgc ccaagagtga gcttgagttt ccagattggg   2040
gtcagccgat gctgagattg gtgttgtggg agtag                              2075
```

```
<210> SEQ ID NO 2
<211> LENGTH: 2404
<212> TYPE: DNA
<213> ORGANISM: Trichoderma reesei
<220> FEATURE:
<221> NAME/KEY: Intron
<222> LOCATION: (159)..(397)
<220> FEATURE:
<221> NAME/KEY: Intron
<222> LOCATION: (475)..(540)
<220> FEATURE:
<221> NAME/KEY: Intron
<222> LOCATION: (624)..(725)
<220> FEATURE:
<221> NAME/KEY: Intron
<222> LOCATION: (774)..(832)
```

```
<220> FEATURE:
<221> NAME/KEY: Intron
<222> LOCATION: (1199)..(1243)
<220> FEATURE:
<221> NAME/KEY: Intron
<222> LOCATION: (1429)..(1506)
<220> FEATURE:
<221> NAME/KEY: Intron
<222> LOCATION: (2123)..(2221)

<400> SEQUENCE: 2
```

| | | | | | |
|---|---|---|---|---|---|
| atgctgttgt | cagcgtccct | ctcggcgttg | gccttggcca | cagtttcact | cgcacagggc | 60 |
| acgacacaca | tccccgtcac | cggtgttccc | gtctctcctg | gtgctgccgt | gccgctgaga | 120 |
| cagaacatca | atgacctggc | caagtccggg | ccgcaatggt | gagtgacgcc | ctccttccac | 180 |
| cacactttac | ctcagtcaag | agacaagagg | gagacaagta | caaagcggat | gaaaagaggt | 240 |
| ggacaagaga | gagagagaga | gaaagtgtgt | gtgtgtatgt | gagagcgaga | gagagagaga | 300 |
| gagacaagag | ctattggatg | gaccaggagc | cagcatggag | aacaggggga | gacttgacga | 360 |
| ttcgaggaga | ggggggctca | catgtgcgtg | cgaataggga | tctctacgtt | caggccatgt | 420 |
| acaacatgtc | caagatggac | tcccatgacc | cgtacagctt | cttccagatt | gccggtaaat | 480 |
| atacatctcg | gcctcctgcg | aggcgacgtg | actctcggag | cttttagtaa | caccagctag | 540 |
| gcatccacgg | cgcaccgtac | attgagtaca | caaggccgg | agcaaagtcg | ggcgatggct | 600 |
| ggctgggcta | ctgccctcac | ggtgtatgtg | tttttgtcca | tcgaggaggg | cgcaagagtt | 660 |
| tcatggactt | gaactcttcg | cccttgttgt | gagccggaaa | tcatcgtctc | tgacagtttc | 720 |
| attaggagga | cctcttcatc | agctggcacc | gcccctatgt | cctgctcttt | gaggtatgat | 780 |
| ttgaccacgc | tggactttga | cctcatacaa | acatcaactg | acatcgttgc | agcaagcctt | 840 |
| ggtctccgtc | gccaagggca | tcgccaactc | gtatccccg | tctgtccgcg | ccaagtacca | 900 |
| ggctgccgcc | gccagcctgc | gcgcccccta | ctgggactgg | gccgcgaca | gctccgtgcc | 960 |
| cgccgtcacc | gtcccccaga | cgctcaagat | caacgtcccc | agcggcagca | gcaccaagac | 1020 |
| cgtcgactac | accaacccgc | tcaagacgta | ctacttcccg | cgcatgtcct | tgaccggctc | 1080 |
| gtacggcgag | ttcaccggcg | gaggcaacga | ccacaccgtc | cgctgcgccg | cctccaagca | 1140 |
| gagctatccc | gccaccgcca | actccaacct | ggctgcccgt | ccttacaagt | cctggatcgt | 1200 |
| acgtagtccc | cctttcccttt | tggaagcttc | cccttgagta | aagctcgtca | ctgacacaga | 1260 |
| gagcggcccg | cagtacgatg | tcctgaccaa | ctctcaaaac | tttgccgact | tcgcctccac | 1320 |
| cagcggcccc | ggcatcaacg | ttgagcagat | ccacaacgcc | atccactggg | acggtgcttg | 1380 |
| cggctcccag | ttcctcgccc | ccgactactc | cggcttcgac | ccctgttgt | aagtcaatcg | 1440 |
| agacgtcaag | agtcatcttg | tcaacaaccg | atggcaaacg | cagtctgtac | tgacgctgca | 1500 |
| aaatagcttc | atgcaccacg | cccaggtcga | ccgcatgtgg | gccttctggg | aggccatcat | 1560 |
| gccctcgtcg | cccctcttca | cggcctcgta | caagggccag | tcgcgcttca | actccaagtc | 1620 |
| gggcagcacc | atcaccccg | actcgcccct | gcagcccttc | taccaggcca | acggcaagtt | 1680 |
| ccacacgtcc | aacacggtca | agagcatcca | gggcatgggc | tactcgtacc | agggcatcga | 1740 |
| gtactggcaa | aagtcccagg | cccagatcaa | gtcgagcgtc | accaccatca | tcaaccagct | 1800 |
| gtacgggccc | aactcgggca | agaagcgcaa | cgccccgcgc | gacttcttga | gcgacattgt | 1860 |
| caccgacgtc | gagaacctca | tcaagacccg | ttactttgcc | aagatctcgg | tcaacgtgac | 1920 |
| cgaggtgacg | gtccgccccg | ccgagatcaa | cgtctacgtc | ggcggccaga | aggccggcag | 1980 |
| cttgatcgtc | atgaagctcc | ccgccgaggg | cacggtcaac | ggcggcttca | ccattgacaa | 2040 |

```
cccatgcaa agcatcctgc acggtggtct ccgcaacgcc gtccaggcct ttaccgagga    2100
cattgaggtt gagattctct ctgtaagttt tccccctct ctccactccc gaccactcac    2160
tgtcactatt tcgactagtc accgtcaaga tgtgtatttg tttgctgacc cccaagcgca    2220
gaaggacgga caagccatcc ccctcgagac ggtccccagc ctgtccatcg acctcgaggt    2280
cgccaacgtc accctgccct ccgccctcga ccagctgccc aagtacggcc agcgctccag    2340
gcaccgcgcc aaggccgccc agcgcggaca ccgctttgcc gttccccata tccctcctct    2400
gtaa                                                                 2404
```

<210> SEQ ID NO 3
<211> LENGTH: 623
<212> TYPE: PRT
<213> ORGANISM: Trichoderma reesei

<400> SEQUENCE: 3

```
Met Gly Phe Leu Ala Arg Leu Thr Trp Val Phe His Leu Val Leu Leu
1               5                   10                  15

Leu Val Ala Ala Gln Asp Tyr Asp Phe Gly Val Asp Val Ile Ser Ile
            20                  25                  30

Thr Arg Arg Arg Asp Thr Asp Ala Pro Ile Val Val Gly Arg Leu Pro
        35                  40                  45

Ser Ala Ser Asn Gly Ser Thr Pro Leu Arg Leu Glu Ile Arg Asp Val
    50                  55                  60

Lys Ala Asp Lys Tyr Arg Trp Asp Leu Tyr Ile Leu Ala Leu Ser Met
65                  70                  75                  80

Phe Gln Ser Val Asn Gln Asp Asp Pro Leu Ser Tyr Tyr Gln Val Ala
                85                  90                  95

Gly Ile His Gly Val Pro Phe Val Thr Trp Asn Gly Val Gly Pro Ala
            100                 105                 110

Ala Gly Ala Ser Gln Ser Gly Tyr Cys Pro His Ser Ser Val Leu Phe
        115                 120                 125

Pro Thr Trp His Arg Pro Tyr Leu Ala Leu Tyr Glu Gln Glu Leu His
    130                 135                 140

Lys Leu Ala Gly Ala Ile Ala Asp Met Phe Ala Asn Ala Thr Glu Arg
145                 150                 155                 160

Phe Leu Tyr Arg Gln Ala Ala Ser Asp Phe Arg Ile Pro Tyr Trp Asp
                165                 170                 175

Trp Ala Ser Pro Ala Pro Glu Gly Glu Ser His Phe Pro Asp Val Phe
            180                 185                 190

Trp Asn Ser Thr Met Ile Gln Tyr Gly Pro Asn Gly Val Gln Val Ile
        195                 200                 205

Arg Asn Pro Leu Tyr Ser Tyr Ser Phe His Pro Leu Asp Gly Asp Ala
    210                 215                 220

Leu Ile Trp Pro Pro Leu Arg Ser Trp Asn Glu Thr Lys Arg Ala Pro
225                 230                 235                 240

Asn Thr Glu Ile Ser Gln Ala Glu Pro Pro Ser Met Asn Asp Gln Val
                245                 250                 255

Ser Ala Ala Leu Leu Ala Arg Leu Pro Glu Ile Gln Gln Arg Leu Tyr
            260                 265                 270

Ile Leu Phe Ser Ser Tyr His Glu Phe Asp Ser Phe Ser Asn Lys Asn
        275                 280                 285

Tyr Ala Phe Ser Gln Asn Leu Ser His Leu Asp Ser Ile Glu Ala Val
    290                 295                 300

His Asp Ile Ile His Ile Tyr Gly Gly Ser Arg Gly His Met Thr Tyr
```

```
            305                 310                 315                 320

Val Pro Leu Ser Ser Phe Asp Pro Leu Phe Leu His His Ala Met
                    325                 330                 335

Thr Asp Arg Leu Ile Ser Met Trp Gln Leu Leu Asn Pro Ser Ala Trp
                340                 345                 350

Met Thr Pro Gln Ile Ser Gly Glu Thr Thr Tyr Thr Ala Leu Lys Gly
                355                 360                 365

Thr Met Gln Asn Ser Ser Thr Pro Leu Thr Pro Phe Met Ser Ser Ala
            370                 375                 380

Asp Gly Thr Phe Trp Asp Ser Asp Met Ser Arg Ser Thr Glu Val Phe
    385                 390                 395                 400

Gly Tyr Ala Tyr Gly Asp Thr Ser Tyr Val Pro Gly Asp Ser Glu Ser
                    405                 410                 415

Pro Arg Asn Lys Leu Ile Arg Lys Ile Asn Arg Trp Leu Gly Leu Asn
                420                 425                 430

Ser Pro Ala Met Val Arg Ile Lys Ser Gln Ala Gln Asn Arg Arg Pro
                435                 440                 445

Ser Gly Val Trp Lys Gly Asn Thr Gly Val Lys Gly Val Gln Pro Ser
        450                 455                 460

Leu Lys Ile Asp Met Ser Asp Val Val Asp Asp His Tyr Thr Glu Trp
    465                 470                 475                 480

Ile Ala Asn Val His Val Asn His Gly Ala Leu Asp Gly Ser Phe Ser
                    485                 490                 495

Ile Tyr Phe Phe Ala Gly Lys Pro Pro Ala Asp Val Gly Thr Trp Ala
                500                 505                 510

Phe Ala Pro Asn Leu Met Gly Ser Val Gly Ile Phe Thr Met Ser Gly
                515                 520                 525

Met Gly Gly His His Ser Lys Met Ser Gly Ser Val Pro Leu Thr Met
            530                 535                 540

Ala Leu Met Arg Leu Ala Ser Leu Gly Ala Val Gln Ser Val Glu Pro
    545                 550                 555                 560

Asn Ser Val Val Ala Phe Leu Gln Ser Arg Leu His Phe Arg Ile Ala
                    565                 570                 575

Ser Ile Asp Asp Lys Glu Ile Asp Pro Ser Leu Val Ala Gly Leu Phe
                580                 585                 590

Ile Gly Ile Ser Ser Thr Arg Val Arg Leu Pro Lys Ser Glu Leu Glu
                595                 600                 605

Phe Pro Asp Trp Gly Pro Met Leu Arg Leu Val Leu Trp Glu
            610                 615                 620

<210> SEQ ID NO 4
<211> LENGTH: 571
<212> TYPE: PRT
<213> ORGANISM: Trichoderma reesei

<400> SEQUENCE: 4

Met Leu Leu Ser Ala Ser Leu Ser Ala Leu Ala Leu Ala Thr Val Ser
1               5                   10                  15

Leu Ala Gln Gly Thr Thr His Ile Pro Val Thr Gly Val Pro Val Ser
            20                  25                  30

Pro Gly Ala Ala Val Pro Leu Arg Gln Asn Ile Asn Asp Leu Ala Lys
        35                  40                  45

Ser Gly Pro Gln Trp Asp Leu Tyr Val Gln Ala Met Tyr Asn Met Ser
    50                  55                  60

Lys Met Asp Ser His Asp Pro Tyr Ser Phe Phe Gln Ile Ala Gly Ile
```

|   |   |   | 65  |   |   |   | 70  |   |   |   | 75  |   |   |   | 80  |
|---|---|---|-----|---|---|---|-----|---|---|---|-----|---|---|---|-----|

His Gly Ala Pro Tyr Ile Glu Tyr Asn Lys Ala Gly Ala Lys Ser Gly
            85             90             95

Asp Gly Trp Leu Gly Tyr Cys Pro His Gly Glu Asp Leu Phe Ile Ser
        100             105            110

Trp His Arg Pro Tyr Val Leu Leu Phe Glu Gln Ala Leu Val Ser Val
    115             120            125

Ala Lys Gly Ile Ala Asn Ser Tyr Pro Ser Val Arg Ala Lys Tyr
130             135            140

Gln Ala Ala Ala Ser Leu Arg Ala Pro Tyr Trp Asp Trp Ala Ala
145          150           155          160

Asp Ser Ser Val Pro Ala Val Thr Val Pro Gln Thr Leu Lys Ile Asn
        165           170            175

Val Pro Ser Gly Ser Ser Thr Lys Thr Val Asp Tyr Thr Asn Pro Leu
        180           185           190

Lys Thr Tyr Tyr Phe Pro Arg Met Ser Leu Thr Gly Ser Tyr Gly Glu
    195             200            205

Phe Thr Gly Gly Gly Asn Asp His Thr Val Arg Cys Ala Ala Ser Lys
210             215            220

Gln Ser Tyr Pro Ala Thr Ala Asn Ser Asn Leu Ala Ala Arg Pro Tyr
225          230           235          240

Lys Ser Trp Ile Leu Val Thr Asp Thr Glu Ser Gly Pro Gln Tyr Asp
        245           250            255

Val Leu Thr Asn Ser Gln Asn Phe Ala Asp Phe Ala Ser Thr Ser Gly
        260           265           270

Pro Gly Ile Asn Val Glu Gln Ile His Asn Ala Ile His Trp Asp Gly
        275           280            285

Ala Cys Gly Ser Gln Phe Leu Ala Pro Asp Tyr Ser Gly Phe Asp Pro
290          295           300

Leu Phe Phe Met His His Ala Gln Val Asp Arg Met Trp Ala Phe Trp
305          310           315          320

Glu Ala Ile Met Pro Ser Ser Pro Leu Phe Thr Ala Ser Tyr Lys Gly
        325           330            335

Gln Ser Arg Phe Asn Ser Lys Ser Gly Ser Thr Ile Thr Pro Asp Ser
        340           345           350

Pro Leu Gln Pro Phe Tyr Gln Ala Asn Gly Lys Phe His Thr Ser Asn
        355           360           365

Thr Val Lys Ser Ile Gln Gly Met Gly Tyr Ser Tyr Gln Gly Ile Glu
    370             375            380

Tyr Trp Gln Lys Ser Gln Ala Gln Ile Lys Ser Ser Val Thr Thr Ile
385          390           395          400

Ile Asn Gln Leu Tyr Gly Pro Asn Ser Gly Lys Lys Arg Asn Ala Pro
        405           410           415

Arg Asp Phe Leu Ser Asp Ile Val Thr Asp Val Glu Asn Leu Ile Lys
        420           425           430

Thr Arg Tyr Phe Ala Lys Ile Ser Val Asn Val Thr Glu Val Thr Val
    435             440            445

Arg Pro Ala Glu Ile Asn Val Tyr Val Gly Gly Gln Lys Ala Gly Ser
    450             455            460

Leu Ile Val Met Lys Leu Pro Ala Glu Gly Thr Val Asn Gly Gly Phe
465          470           475          480

Thr Ile Asp Asn Pro Met Gln Ser Ile Leu His Gly Gly Leu Arg Asn
        485           490           495

```
Ala Val Gln Ala Phe Thr Glu Asp Ile Glu Val Glu Ile Leu Ser Lys
                500                 505                 510

Asp Gly Gln Ala Ile Pro Leu Glu Thr Val Pro Ser Leu Ser Ile Asp
        515                 520                 525

Leu Glu Val Ala Asn Val Thr Leu Pro Ser Ala Leu Asp Gln Leu Pro
    530                 535                 540

Lys Tyr Gly Gln Arg Ser Arg His Arg Ala Lys Ala Ala Gln Arg Gly
545                 550                 555                 560

His Arg Phe Ala Val Pro His Ile Pro Pro Leu
                565                 570

<210> SEQ ID NO 5
<211> LENGTH: 33
<212> TYPE: DNA
<213> ORGANISM: Artificial
<220> FEATURE:
<223> OTHER INFORMATION: synthetic primer

<400> SEQUENCE: 5
gctaccgcgg atgggcttcc tcgctcgcct cac                              33

<210> SEQ ID NO 6
<211> LENGTH: 55
<212> TYPE: DNA
<213> ORGANISM: Artificial
<220> FEATURE:
<223> OTHER INFORMATION: synthetic primer

<400> SEQUENCE: 6
ctgaggatcc tcagtggtgg tggtggtggt gctcccacaa caccaatctc agcat      55

<210> SEQ ID NO 7
<211> LENGTH: 55
<212> TYPE: DNA
<213> ORGANISM: Artificial
<220> FEATURE:
<223> OTHER INFORMATION: synthetic primer

<400> SEQUENCE: 7
ggggacaagt ttgtacaaaa aagcaggcta tcatgctgtt gtcaggtccc tctcg      55

<210> SEQ ID NO 8
<211> LENGTH: 76
<212> TYPE: DNA
<213> ORGANISM: Artificial
<220> FEATURE:
<223> OTHER INFORMATION: synthetic primer

<400> SEQUENCE: 8
ggggaccact ttgtacaaga aagctgggtc agtggtggtg gtggtggtgc agaggaggga 60
tatggggaac ggcaaa                                                 76

<210> SEQ ID NO 9
<211> LENGTH: 434
<212> TYPE: PRT
<213> ORGANISM: Trichoderma reesei

<400> SEQUENCE: 9

Met Gly Phe Leu Ala Arg Leu Thr Trp Val Phe His Leu Val Leu Leu
1               5                   10                  15

Leu Val Ala Ala Gln Asp Tyr Asp Phe Gly Val Asp Val Ile Ser Ile
            20                  25                  30

Thr Arg Arg Arg Asp Thr Asp Ala Pro Ile Val Val Gly Arg Leu Pro
```

```
                    35                  40                  45
Ser Ala Ser Asn Gly Ser Thr Pro Leu Arg Leu Glu Ile Arg Asp Val
 50                  55                  60

Lys Ala Asp Lys Tyr Arg Trp Asp Leu Tyr Ile Leu Ala Leu Ser Met
 65                  70                  75                  80

Phe Gln Ser Val Asn Gln Asp Pro Leu Ser Tyr Gln Val Ala
                     85                  90                  95

Gly Ile His Gly Val Pro Phe Val Thr Trp Asn Gly Val Gly Pro Ala
                100                 105                 110

Ala Gly Ala Ser Gln Ser Gly Tyr Cys Pro His Ser Ser Val Leu Phe
                115                 120                 125

Pro Thr Trp His Arg Pro Tyr Leu Ala Leu Tyr Glu Gln Glu Leu His
                130                 135                 140

Lys Leu Ala Gly Ala Ile Ala Asp Met Phe Ala Asn Ala Thr Glu Arg
145                 150                 155                 160

Phe Leu Tyr Arg Gln Ala Ala Ser Asp Phe Arg Ile Pro Tyr Trp Asp
                165                 170                 175

Trp Ala Ser Pro Ala Pro Glu Gly Glu Ser His Phe Pro Asp Val Phe
                180                 185                 190

Trp Asn Ser Thr Met Ile Gln Tyr Gly Pro Asn Gly Val Gln Val Ile
                195                 200                 205

Arg Asn Pro Leu Tyr Ser Tyr Ser Phe His Pro Leu Asp Gly Asp Ala
210                 215                 220

Leu Ile Trp Pro Pro Leu Arg Ser Trp Asn Glu Thr Lys Arg Ala Pro
225                 230                 235                 240

Asn Thr Glu Ile Ser Gln Ala Glu Pro Pro Ser Met Asn Asp Gln Val
                245                 250                 255

Ser Ala Ala Leu Leu Ala Arg Leu Pro Glu Ile Gln Gln Arg Leu Tyr
                260                 265                 270

Ile Leu Phe Ser Ser Tyr His Glu Phe Asp Ser Phe Ser Asn Lys Asn
                275                 280                 285

Tyr Ala Phe Ser Gln Asn Leu Ser His Leu Asp Ser Ile Glu Ala Val
                290                 295                 300

His Asp Ile Ile His Ile Tyr Gly Gly Ser Arg Gly His Met Thr Tyr
305                 310                 315                 320

Val Pro Leu Ser Ser Phe Asp Pro Leu Phe Phe Leu His His Ala Met
                325                 330                 335

Thr Asp Arg Leu Ile Ser Met Trp Gln Leu Leu Asn Pro Ser Ala Trp
                340                 345                 350

Met Thr Pro Gln Ile Ser Gly Glu Thr Thr Tyr Thr Ala Leu Lys Gly
                355                 360                 365

Thr Met Gln Asn Ser Ser Thr Pro Leu Thr Pro Phe Met Ser Ser Ala
370                 375                 380

Asp Gly Thr Phe Trp Asp Ser Asp Met Ser Arg Ser Thr Glu Val Phe
385                 390                 395                 400

Gly Tyr Ala Tyr Gly Asp Thr Ser Tyr Val Pro Gly Asp Ser Glu Ser
                405                 410                 415

Pro Arg Asn Lys Leu Ile Arg Lys Ile Asn Arg Trp Leu Gly Leu Asn
                420                 425                 430

Ser Pro

<210> SEQ ID NO 10
<211> LENGTH: 410
<212> TYPE: PRT
```

<213> ORGANISM: Trichoderma reesei

<400> SEQUENCE: 10

```
Met Leu Leu Ser Ala Ser Leu Ser Ala Leu Ala Leu Ala Thr Val Ser
1               5                   10                  15

Leu Ala Gln Gly Thr Thr His Ile Pro Val Thr Gly Val Pro Val Ser
                20                  25                  30

Pro Gly Ala Ala Val Pro Leu Arg Gln Asn Ile Asn Asp Leu Ala Lys
            35                  40                  45

Ser Gly Pro Gln Trp Asp Leu Tyr Val Gln Ala Met Tyr Asn Met Ser
        50                  55                  60

Lys Met Asp Ser His Asp Pro Tyr Ser Phe Phe Gln Ile Ala Gly Ile
65                  70                  75                  80

His Gly Ala Pro Tyr Ile Glu Tyr Asn Lys Ala Gly Ala Lys Ser Gly
                85                  90                  95

Asp Gly Trp Leu Gly Tyr Cys Pro His Gly Glu Asp Leu Phe Ile Ser
            100                 105                 110

Trp His Arg Pro Tyr Val Leu Leu Phe Glu Gln Ala Leu Val Ser Val
        115                 120                 125

Ala Lys Gly Ile Ala Asn Ser Tyr Pro Pro Ser Val Arg Ala Lys Tyr
130                 135                 140

Gln Ala Ala Ala Ser Leu Arg Ala Pro Tyr Trp Asp Trp Ala Ala
145                 150                 155                 160

Asp Ser Ser Val Pro Ala Val Thr Val Pro Gln Thr Leu Lys Ile Asn
                165                 170                 175

Val Pro Ser Gly Ser Ser Thr Lys Thr Val Asp Tyr Thr Asn Pro Leu
            180                 185                 190

Lys Thr Tyr Tyr Phe Pro Arg Met Ser Leu Thr Gly Ser Tyr Gly Glu
        195                 200                 205

Phe Thr Gly Gly Asn Asp His Thr Val Arg Cys Ala Ala Ser Lys
210                 215                 220

Gln Ser Tyr Pro Ala Thr Ala Asn Ser Asn Leu Ala Ala Arg Pro Tyr
225                 230                 235                 240

Lys Ser Trp Ile Leu Val Thr Asp Thr Glu Ser Gly Pro Gln Tyr Asp
                245                 250                 255

Val Leu Thr Asn Ser Gln Asn Phe Ala Asp Phe Ala Ser Thr Ser Gly
            260                 265                 270

Pro Gly Ile Asn Val Glu Gln Ile His Asn Ala Ile His Trp Asp Gly
        275                 280                 285

Ala Cys Gly Ser Gln Phe Leu Ala Pro Asp Tyr Ser Gly Phe Asp Pro
290                 295                 300

Leu Phe Phe Met His His Ala Gln Val Asp Arg Met Trp Ala Phe Trp
305                 310                 315                 320

Glu Ala Ile Met Pro Ser Ser Pro Leu Phe Thr Ala Ser Tyr Lys Gly
                325                 330                 335

Gln Ser Arg Phe Asn Ser Lys Ser Gly Ser Thr Ile Thr Pro Asp Ser
            340                 345                 350

Pro Leu Gln Pro Phe Tyr Gln Ala Asn Gly Lys Phe His Thr Ser Asn
        355                 360                 365

Thr Val Lys Ser Ile Gln Gly Met Gly Tyr Ser Tyr Gln Gly Ile Glu
370                 375                 380

Tyr Trp Gln Lys Ser Gln Ala Gln Ile Lys Ser Ser Val Thr Thr Ile
385                 390                 395                 400
```

```
Ile Asn Gln Leu Tyr Gly Pro Asn Ser Gly
            405                 410
```